(12) United States Patent
Legrand

(10) Patent No.: US 7,550,015 B2
(45) Date of Patent: Jun. 23, 2009

US007550015B2

(54) DYE COMPOSITION WITH A REDUCED CONTENT OF STARTING MATERIALS, AND PROCESS FOR DYEING KERATIN FIBERS USING THE SAME

(75) Inventor: Frédéric Legrand, Tokyo (JP)

(73) Assignee: L'Oreal S.A., Paris (FR)

( * ) Notice: Subject to any disclaimer, the term of this patent is extended or adjusted under 35 U.S.C. 154(b) by 202 days.

(21) Appl. No.: 11/393,700

(22) Filed: Mar. 31, 2006

(65) Prior Publication Data

US 2006/0248662 A1  Nov. 9, 2006

Related U.S. Application Data

(60) Provisional application No. 60/681,156, filed on May 16, 2005.

(30) Foreign Application Priority Data

Mar. 31, 2005  (FR) ................... 05 50835

(51) Int. Cl.
*A61Q 5/10* (2006.01)
(52) U.S. Cl. .............. 8/405; 8/406; 8/407; 8/435; 8/552; 8/554; 8/559
(58) Field of Classification Search .......... 8/405, 8/406, 407, 435, 552, 554, 559
See application file for complete search history.

(56) References Cited

U.S. PATENT DOCUMENTS

| | | | |
|---|---|---|---|
| 2,261,002 A | 10/1941 | Ritter | |
| 2,271,378 A | 1/1942 | Searle | |
| 2,273,780 A | 2/1942 | Dittmar | |
| 2,375,853 A | 5/1945 | Kirby et al. | |
| 2,388,614 A | 11/1945 | Kirby et al. | |
| 2,454,547 A | 11/1948 | Bock et al. | |
| 2,961,347 A | 11/1960 | Floyd | |
| 3,206,462 A | 9/1965 | McCarty | |
| 3,227,615 A | 1/1966 | Korden | |
| 3,472,840 A | 10/1969 | Stone et al. | |
| 3,632,559 A | 1/1972 | Matter et al. | |
| 3,836,537 A | 9/1974 | Boerwinkle et al. | |
| 3,874,870 A | 4/1975 | Green et al. | |
| 3,910,862 A | 10/1975 | Barabas et al. | |
| 3,912,808 A | 10/1975 | Sokol | |
| 3,917,817 A | 11/1975 | Varlerberghe et al. | |
| 3,929,990 A | 12/1975 | Green et al. | |
| 3,966,904 A | 6/1976 | Green et al. | |
| 3,986,825 A | 10/1976 | Sokol | |
| 4,001,432 A | 1/1977 | Green et al. | |
| 4,005,193 A | 1/1977 | Green et al. | |
| 4,013,787 A | 3/1977 | Varlerberghe et al. | |
| 4,025,617 A | 5/1977 | Green et al. | |
| 4,025,627 A | 5/1977 | Green et al. | |
| 4,025,653 A | 5/1977 | Green et al. | |
| 4,026,945 A | 5/1977 | Green et al. | |
| 4,027,008 A | 5/1977 | Sokol | |
| 4,027,020 A | 5/1977 | Green et al. | |
| 4,031,307 A | 6/1977 | DeMartino et al. | |
| 4,075,136 A | 2/1978 | Schaper | |
| 4,116,894 A | 9/1978 | Lentz et al. | |
| 4,131,576 A | 12/1978 | Iovine et al. | |
| 4,157,388 A | 6/1979 | Christiansen | |
| 4,165,367 A | 8/1979 | Chakrabarti | |
| 4,166,894 A | 9/1979 | Schaper | |
| 4,172,887 A | 10/1979 | Vanlerberghe et al. | |
| 4,189,468 A | 2/1980 | Vanlerberghe et al. | |
| 4,197,865 A | 4/1980 | Jacquet et al. | |
| 4,217,914 A | 8/1980 | Jacquet et al. | |
| 4,223,009 A | 9/1980 | Chakrabarti | |
| 4,240,450 A | 12/1980 | Grollier et al. | |
| 4,277,581 A | 7/1981 | Vanlerberghe et al. | |

(Continued)

FOREIGN PATENT DOCUMENTS

DE  30 30 119  11/1987

(Continued)

OTHER PUBLICATIONS

French Search Report for FR 0550835, dated Nov. 3, 2005.

(Continued)

*Primary Examiner*—Eisa B Elhilo
(74) *Attorney, Agent, or Firm*—Finnegan, Henderson, Farabow, Garrett & Dunner, LLP

(57) ABSTRACT

The present disclosure relates to a dye composition comprising water in an amount of at least 40% by weight, relative to the total weight of the dye composition. The present disclosure also relates to a process for dyeing keratin fibers, such as human keratin fibers, using the dye composition as disclosed herein. The dye composition also comprises at least one dye chosen from oxidation dye precursors and direct dyes; at least one surfactant chosen from nonionic and anionic surfactants; at least one hydroxyethylcelluloses; at least one fatty substance; wherein the weight ratio of the total amount of surfactants to the total amount of the at least one fatty substance is greater than or equal to 1.75; and also comprising at least one cationic associative polymer. The present disclosure also relates to a multi-compartment kit comprising a first compartment comprising at least one dye composition as disclosed herein, and a second compartment comprising at least one, oxidizing composition.

29 Claims, No Drawings

U.S. PATENT DOCUMENTS

| | | | |
|---|---|---|---|
| 4,348,202 | A | 9/1982 | Grollier et al. |
| 4,349,532 | A | 9/1982 | Vanlerberghe et al. |
| 4,381,919 | A | 5/1983 | Jacquet et al. |
| 4,422,853 | A | 12/1983 | Jacquet et al. |
| 4,445,521 | A | 5/1984 | Grollier et al. |
| 4,579,732 | A | 4/1986 | Grollier et al. |
| 4,591,610 | A | 5/1986 | Grollier |
| 4,608,250 | A | 8/1986 | Jacquet et al. |
| 4,702,906 | A | 10/1987 | Jacquet et al. |
| 4,719,099 | A | 1/1988 | Grollier et al. |
| 4,719,282 | A | 1/1988 | Nadolsky et al. |
| 4,761,273 | A | 8/1988 | Grollier et al. |
| 4,777,040 | A | 10/1988 | Grollier et al. |
| 4,803,221 | A | 2/1989 | Bair |
| 4,839,166 | A | 6/1989 | Grollier et al. |
| 4,919,923 | A | 4/1990 | Hoeffkes et al. |
| 4,948,579 | A | 8/1990 | Jacquet et al. |
| 4,970,066 | A | 11/1990 | Grollier et al. |
| 4,996,059 | A | 2/1991 | Grollier et al. |
| 5,009,880 | A | 4/1991 | Grollier et al. |
| 5,057,311 | A | 10/1991 | Kamegai et al. |
| 5,089,252 | A | 2/1992 | Grollier et al. |
| 5,139,037 | A | 8/1992 | Grollier et al. |
| 5,196,189 | A | 3/1993 | Jacquet et al. |
| 5,480,459 | A | 1/1996 | Mager et al. |
| 5,494,489 | A | 2/1996 | Akram et al. |
| 5,708,151 | A | 1/1998 | Mockli |
| 5,792,221 | A | 8/1998 | Lagrange et al. |
| 5,958,392 | A | 9/1999 | Grollier et al. |
| 5,990,233 | A | 11/1999 | Barron et al. |
| 6,106,578 | A | 8/2000 | Jones |
| 6,436,151 | B2 * | 8/2002 | Cottard et al. ............... 8/406 |
| 6,540,791 | B1 | 4/2003 | Dias |
| 6,613,315 | B1 | 9/2003 | Dupuis |
| 6,800,098 | B1 | 10/2004 | Allard et al. |
| 6,824,570 | B2 | 11/2004 | Vidal et al. |
| 6,881,230 | B2 | 4/2005 | Vidal |
| 6,884,265 | B2 | 4/2005 | Vidal et al. |
| 6,884,267 | B2 | 4/2005 | Vidal et al. |
| 6,893,471 | B2 | 5/2005 | Vidal |
| 7,001,436 | B2 | 2/2006 | Vidal et al. |
| 7,022,143 | B2 | 4/2006 | Vidal et al. |
| 7,060,110 | B2 | 6/2006 | Vidal et al. |
| 7,077,873 | B2 | 7/2006 | David et al. |
| 7,261,743 | B2 | 8/2007 | Plos et al. |
| 2001/0023514 | A1 | 9/2001 | Cottard et al. |
| 2002/0095732 | A1 | 7/2002 | Kravtchenko et al. |
| 2003/0084516 | A9 | 5/2003 | Kravtchenko et al. |
| 2003/0106169 | A1 | 6/2003 | Vidal et al. |
| 2003/0124079 | A1 | 7/2003 | Mougin et al. |
| 2003/0192134 | A1 | 10/2003 | Desenne et al. |
| 2004/0047821 | A1 | 3/2004 | Maubru et al. |
| 2004/0060126 | A1 | 4/2004 | Cottard et al. |
| 2004/0093675 | A1 | 5/2004 | Vidal et al. |
| 2004/0093676 | A1 | 5/2004 | Vidal et al. |
| 2004/0098815 | A1 | 5/2004 | Schmenger et al. |
| 2004/0107513 | A1 | 6/2004 | Vidal et al. |
| 2004/0127692 | A1 | 7/2004 | David et al. |
| 2004/0133995 | A1 | 7/2004 | Cottard et al. |
| 2004/0141943 | A1 | 7/2004 | Mougin et al. |
| 2004/0143911 | A1 | 7/2004 | Vidal |
| 2004/0168263 | A1 | 9/2004 | Vidal |
| 2004/0172771 | A1 | 9/2004 | Cottard et al. |
| 2004/0180030 | A1 | 9/2004 | Maubru |
| 2004/0187225 | A1 | 9/2004 | Vidal et al. |
| 2004/0200009 | A1 | 10/2004 | Vidal |
| 2004/0205902 | A1 | 10/2004 | Cottard et al. |
| 2004/0216246 | A1 | 11/2004 | Cotteret et al. |
| 2004/0244123 | A1 | 12/2004 | Vidal et al. |
| 2005/0000039 | A1 | 1/2005 | Audosset |
| 2005/0039268 | A1 | 2/2005 | Plos et al. |

FOREIGN PATENT DOCUMENTS

| | | |
|---|---|---|
| DE | 38 34 142 | 4/1990 |
| DE | 41 27 230 | 2/1993 |
| DE | 41 03 292 | 2/1994 |
| DE | 101 32 915 | 1/2003 |
| EP | 0 080 976 B1 | 9/1986 |
| EP | 0 122 324 B1 | 1/1988 |
| EP | 0 412 706 | 2/1991 |
| EP | 0 337 354 B1 | 2/1994 |
| EP | 0 714 954 B1 | 6/1996 |
| EP | 0 825 200 A1 | 2/1998 |
| EP | 1 048 289 | 11/2000 |
| EP | 1 142 555 | 10/2001 |
| EP | 1 174 450 A1 | 1/2002 |
| EP | 0 824 914 B1 | 2/2002 |
| EP | 1 232 739 | 8/2002 |
| EP | 1 413 287 | 4/2004 |
| EP | 1 426 032 A2 | 6/2004 |
| EP | 1 426 039 | 6/2004 |
| EP | 1 428 506 A1 | 6/2004 |
| EP | 1 473 025 A1 | 11/2004 |
| EP | 1 518 547 | 3/2005 |
| FR | 1 400 366 | 4/1965 |
| FR | 1 492 597 | 7/1967 |
| FR | 1 583 363 | 10/1969 |
| FR | 2 077 143 | 9/1971 |
| FR | 2 080 759 | 11/1971 |
| FR | 2 162 025 | 7/1973 |
| FR | 2 190 406 | 2/1974 |
| FR | 2 252 840 | 6/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 598 611 | 11/1987 |
| FR | 2 692 572 | 12/1993 |
| FR | 2 717 076 | 9/1995 |
| FR | 2 795 312 | 12/2000 |
| FR | 2 803 195 | 7/2001 |
| FR | 2 807 650 | 10/2001 |
| FR | 2 822 693 | 10/2002 |
| FR | 2 822 694 | 10/2002 |
| FR | 2 822 696 | 10/2002 |
| FR | 2 822 698 | 10/2002 |
| FR | 2 825 625 | 12/2002 |
| FR | 2 825 702 | 12/2002 |
| FR | 2 829 926 | 3/2003 |
| FR | 2 833 833 | 6/2003 |
| FR | 2 844 269 | 3/2004 |
| GB | 1 021 400 | 3/1966 |
| GB | 1 331 819 | 9/1973 |
| GB | 1 347 051 | 2/1974 |
| GB | 1 479 786 | 7/1977 |
| GB | 1 546 809 | 5/1979 |
| WO | WO 95/01772 | 1/1995 |
| WO | WO 95/15144 | 6/1995 |
| WO | WO 99/40893 | 8/1999 |
| WO | WO 00/68282 | 11/2000 |
| WO | WO 02/30370 | 4/2002 |
| WO | WO 02/45674 A1 | 6/2002 |
| WO | WO 02/074271 | 9/2002 |

| | | | |
|---|---|---|---|
| WO | WO 02/078 660 A1 | 10/2002 | |
| WO | WO 02/100 369 A2 | 12/2002 | |
| WO | WO 02/100 834 A1 | 12/2002 | |

OTHER PUBLICATIONS

English Language Derwent Abstract for EP 0 080 976, Sep. 1986.
English Language Derwent Abstract for FR 2 336 434, Jul. 1977.
De Bruin, "Hydrophobically Modified Cellulose Ether for Personal Care." SOFW-Journal Seifen, Oele, Fette, Wachse, Verlag fur Chemische Industri, Augsburg, DE, vol. 120, No. 15, Nov. 30, 1994, pp. 944-946, 948. Reprint by Hercules International Ltd., Aqualon Division, pp. 1-6 [online], http://www.herc.com/aqualon/product_data/tech/62050e1.pdf (1994).
Copending U.S. Appl. No. 11/393,694, filed Mar. 31, 2006.
Copending U.S. Appl. No. 11/393,696, filed Mar. 31, 2006.
Copending U.S. Appl. No. 11/393,698, filed Mar. 31, 2006.
Copending U.S. Appl. No. 11/393,701, filed Mar. 31, 2006.
Copending U.S. Appl. No. 11/394,234, filed Mar. 31, 2006.
English language Derwent Abstract of EP 1 048 289, dated Nov. 2, 2000.
English language Derwent Abstract of DE 101 32 915, dated Jan. 30, 2003.
English language Derwent Abstract of DE 30 30 119, dated Nov. 19, 1987.
English language Derwent Abstract of DE 38 34 142, dated Apr. 12, 1990.
English language Derwent Abstract of DE 41 03 292, dated Feb. 10, 1994.
English language Derwent Abstract of DE 41 27 230, dated Feb. 18, 1993.
English language Derwent Abstract of EP 1 232 739, dated Aug. 21, 2002.
English language Derwent Abstract of EP 1 518 547, dated Mar. 30, 2005.
English language Derwent Abstract of FR 2 795 312, dated Dec. 29, 2000.
European Search Report for EP 06 11 1856 (corresponding European counterpart application to U.S. Appl. No. 11/394,234, dated Jul. 19, 2006.
European Search Report for EP 06 11 1858 (corresponding European counterpart application to U.S. Appl. No. 11/393,698, dated Jul. 19, 2006.
European Search Report for EP 06 11 1860 (corresponding European counterpart application to U.S. Appl. No. 11/393,701, dated Jul. 18, 2006.
European Search Report for EP 06111861.8 (corresponding European counterpart application to U.S. Appl. No. 11/393,694, dated Jun. 14, 2006.
French Search Report for FR 05/50837 for U.S. Appl. No. 11/393,694, dated Nov. 10, 2005.
French Search Report for FR 05/50838 for U.S. Appl. No. 11/393,698, dated Nov. 4, 2005.
French Search Report for FR 05/50839 for U.S. Appl. No. 11/393,701, dated Nov. 9, 2005.
French Search Report for FR 05/50841 for U.S. Appl. No. 11/393,696, dated Feb. 14, 2006.
French Search Report for FR 05/50842 for U.S. Appl. No. 11/394,234, dated Feb. 15, 2006.
G. Fonnum, J. Bakke and Fk. Hansen—Colloid Polym. Sci. 271, 380-389 (1993).
International Search report for PCT/EP2006/002588, dated Jul. 4, 2006, for corresponding U.S. Appl. No. 11/795,641.
Office Action mailed Jan. 7, 2008, in co-pending U.S. Appl. No. 11/393,694.
Office Action mailed Jan. 7, 2008, in co-pending U.S. Appl. No. 11/393,696.
Office Action mailed Jan. 7, 2008, in co-pending U.S. Appl. No. 11/393,698.
Office Action mailed Jan. 7, 2008, in co-pending U.S. Appl. No. 11/393,701.
Office Action mailed Jan. 7, 2008, in co-pending U.S. Appl. No. 11/394,234.
Office Action mailed Jun. 13, 2008, in co-pending U.S. Appl. No. 11/393,698.
Office Action mailed Jun. 23, 2008, in co-pending U.S. Appl. No. 11/393,694.
Office Action mailed Jun. 23, 2008, in co-pending U.S. Appl. No. 11/394,234.
Office Action mailed Jun. 27, 2008, in co-pending U.S. Appl. No. 11/393,701.
Office Action mailed Oct. 22, 2008, in co-pending U.S. Appl. No. 11/393,698.

* cited by examiner

DYE COMPOSITION WITH A REDUCED CONTENT OF STARTING MATERIALS, AND PROCESS FOR DYEING KERATIN FIBERS USING THE SAME

This application claims benefit of U.S. Provisional Application No. 60/681,156, filed May 16, 2005, the contents of which are incorporated herein by reference. This application also claims benefit of priority under 35 U.S.C. § 119 to French Patent Application No. FR 05 50835, filed Mar. 31, 2005, the contents of which are also incorporated herein by reference.

The present disclosure relates to a dye composition comprising water in an amount of at least 40% by weight, relative to the total weight of the composition, and also relates to a process for dyeing keratin fibers, such as human keratin fibers, using such a composition. The present disclosure similarly relates to a multi-compartment kit comprising, for example, a dye composition in a first compartment, and an oxidizing composition in a second compartment.

There are essentially two methods for dyeing of keratin fibers, for instance for dyeing human keratin fibers such as the hair.

The first, known as oxidation dyeing or permanent dyeing, comprises using oxidation dye precursors, which are colorless or sparingly colored compounds. When they are placed in contact with an oxidizing agent, these compounds produce, via a process of oxidative condensation taking place within the fiber itself, colored substances that remain trapped in the fibers.

The second, known as direct dyeing or semi-permanent dyeing, comprises using colored and coloring compounds that have an affinity for the keratin fibers onto which they are applied. This type of dyeing does not require the use of an oxidizing agent to reveal the color, although it is not excluded for this type of agent to be present during the direct dyeing process. The latter case is then referred to as lightening direct dyeing.

The dye compositions of the prior art are, in the majority of cases, in the form of liquids, gels or creams, which are mixed, if necessary, before being applied to fibers, with an oxidizing composition.

Dye compositions are usually relatively rich in starting materials, among which are usually found fatty substances, surfactants and/or polymers. These compositions can be formulated such that they have spreading properties and textures that are easy to work in order to allow quick and easy application to fibers, while at the same time being thick enough not to run beyond the areas that it is desired to color. Furthermore, these compositions should ideally remain stable during the leave-on time on the fibers and should ideally be easy to remove by rinsing once the desired coloration has been obtained.

It is not uncommon to find that large amounts of starting materials may penalize the dyeing qualities of such compositions. Less favorable kinetics, a reduced intensity of the shade obtained, poorer homogeneity of the color from one fiber to another and/or depending on the location of the fiber (root/end), etc. may thus be observed.

Thus, the present disclosure proposes dye compositions that avoid at least one of the above-mentioned drawbacks, while at the same time preserving at least one of the beneficial properties mentioned above.

Accordingly, one embodiment of the present disclosure relates to dye compositions comprising, in a medium that is suitable for dyeing keratin fibers:

at least one dye chosen from oxidation dye precursors and direct dyes;

at least one surfactant chosen from nonionic and anionic surfactants;

at least one hydroxyethylcellulose;

at least one cationic associative polymer;

at least one fatty substance;

wherein the weight ratio of the total amount of surfactants to the total amount of fatty substances is greater than or equal to 1.75; and wherein the dye composition comprises water in an amount of at least 40% by weight, relative to the total weight of the dye composition.

Another aspect of the present disclosure is a process for dyeing keratin fibers using such a composition, where appropriate, in the presence of an oxidizing composition.

The present disclosure also relates to a multi-compartment kit comprising a first compartment comprising a dye composition according to the present disclosure and further comprising a second compartment comprising an oxidizing composition.

The composition according to the present disclosure can cause less degradation of the dyeing properties and can therefore allow for stronger, more homogeneous and more chromatic colorations to be obtained, while at the same time giving the treated fibers good cosmetic properties and limiting the degradation.

Moreover, the compositions in accordance with the present disclosure may have an ideal texture for use in the dyeing of human keratin fibers, such as in the dyeing of human hair. For example, they may be creamy, thick enough for quick and easy application, with good removal by rinsing, without, however, running beyond the areas of the hair that the dye composition is desired to treat.

Other characteristics and benefits of the present disclosure will emerge more clearly on reading the description and the examples that follow.

As disclosed herein, and unless otherwise indicated, it is pointed out that the limits of ranges of values are included in these ranges.

When mention is made herein of a compound with a fatty chain, it is understood that this chain is a linear or branched, saturated or unsaturated hydrocarbon-based chain containing from 8 to 30 carbon atoms, for example containing from 10 to 24 carbon atoms.

Furthermore, the present disclosure is suitable for dyeing keratin fibers, for instance human keratin fibers, such as the hair.

Thus, as disclosed above, the dye composition according to the present disclosure comprises water in an amount of at least 40% by weight, relative to the total weight of the dye composition.

According to at least one embodiment of the present disclosure, the amount of water in the composition is at least 45% by weight, relative to the total weight of the dye composition.

In accordance with another embodiment of the present disclosure, the amount of water in the composition is at least 50% by weight, relative to the total weight of the dye composition.

Nonionic and Anionic Surfactants

The composition according to the present disclosure can comprise at least one surfactant chosen from nonionic surfactants and anionic surfactants.

For instance, the at least one nonionic surfactant can be chosen from, but is not limited to:
- oxyalkylenated or glycerolated fatty alcohols;
- oxyalkylenated alkylphenols in which the alkyl chain is of $C_8$-$C_{18}$;
- oxyalkylenated or glycerolated fatty amides;
- oxyalkylenated plant oils;
- optionally oxyalkylenated $C_6$-$C_{30}$ acid esters of sorbitan;
- optionally oxyalkylenated fatty acid esters of sucrose;
- fatty acid esters of polyethylene glycol;
- ($C_6$-$C_{30}$)alkylpolyglycosides;
- N—($C_6$-$C_{30}$)alkylglucamine derivatives;
- amine oxides such as ($C_{10}$-$C_{14}$)alkylamine oxides or N-acylaminopropylmorpholine oxides;
- copolymers of ethylene oxide and of propylene oxide;
- mixtures thereof.

According to the present disclosure, the mean number of oxyalkylene units can range from 2 to 150 units. In at least one embodiment, the units are chosen from oxyethylene and oxypropylene units.

As disclosed herein, the polyglycerolated surfactants can comprise on average 1 to 20, for example 1.5 to 5, glycerol groups.

In accordance with at least one embodiment of the present disclosure, the composition comprises at least one nonionic surfactant that can be chosen from oxyalkylenated or glycerolated $C_6$-$C_{30}$ alcohols.

As disclosed herein, the at least one anionic surfactant can be chosen from, but is not limited to:
- ($C_6$-$C_{30}$)alkyl sulfates, ($C_6$-$C_{30}$)alkyl ether sulfates, ($C_6$-$C_{30}$)alkylamido ether sulfates, alkylaryl polyether sulfates, monoglyceride sulfates;
- ($C_6$-$C_{30}$)alkylsulfonates, ($C_6$-$C_{30}$)alkylamide sulfonates, ($C_6$-$C_{30}$)alkylaryl sulfonates, α-olefin sulfonates, paraffin sulfonates;
- ($C_6$-$C_{30}$)alkyl phosphates;
- ($C_6$-$C_{30}$)alkyl sulfosuccinates, ($C_6$-$C_{30}$)alkyl ether sulfosuccinates, ($C_6$-$C_{30}$)alkylamide sulfosuccinates;
- ($C_6$-$C_{30}$)alkyl sulfoacetates;
- ($C_6$-$C_{24}$)acyl sarcosinates;
- ($C_6$-$C_{24}$)acyl glutamates;
- ($C_6$-$C_{30}$)alkylpolyglycoside carboxylic ethers; ($C_6$-$C_{30}$) alkylpolyglycoside sulfosuccinates;
- ($C_6$-$C_{30}$)alkyl sulfosuccinamates;
- ($C_6$-$C_{24}$)acyl isethionates;
- N—($C_6$-$C_{24}$)acyl taurates;
- fatty acid salts; coconut oil acid salts or hydrogenated coconut oil acid salts;
- ($C_8$-$C_{20}$)acyl lactylates;
- ($C_6$-$C_{30}$)alkyl-D-galactoside uronic acid salts; and
- polyoxyalkylenated ($C_6$-$C_{30}$)alkyl ether carboxylic acid salts, polyoxyalkylenated ($C_6$-$C_{30}$)alkylaryl ether carboxylic acid salts, polyoxyalkylenated ($C_6$-$C_{30}$)alkylamido ether carboxylic acid salts;
- and mixtures thereof.

In at least one embodiment, the anionic surfactants are in the form of salts such as salts of alkali metals, for instance sodium; salts of alkaline-earth metals, for instance magnesium; ammonium salts; amine salts; and amino alcohol salts. Depending on the conditions, they may also be in the acid form.

It should be noted that the alkyl or acyl radicals of these various compounds can contain from 12 to 20 carbon atoms. And, for instance, the aryl radical can be chosen from a phenyl or benzyl group.

Furthermore, the polyoxyalkylenated anionic surfactants can, for example, comprise from 2 to 50 alkylene oxide, for instance ethylene oxide, groups.

In accordance with at least one embodiment of the present disclosure, the anionic surfactant can be chosen from fatty acid salts.

According to one embodiment of the present disclosure, the total amount of the at least one surfactant chosen from nonionic surfactants and anionic surfactants ranges from 0.01% to 50% by weight, relative to the weight of the dye composition, for example, from 0.5% to 40% by weight, relative to the total weight of the dye composition.

Hydroxycellulose

At least one hydroxyethylcellulose is also among the ingredients of the composition according to the present disclosure. In at least one embodiment, the molecular weight of the hydroxyethylcellulose is at least 700,000, for example at least $10^6$. The molecular weight may be determined by means of several techniques, including gel permeation chromatography and size exclusion chromatography.

As disclosed herein, suitable compounds include but are not limited to hydroxyethylcellulose with a molecular weight of $1.3 \times 10^6$, sold, for example, under the trade name NATROSOL 250 HHR by the company Aqualon (Hercules), hydroxyethylcellulose with a molecular weight of $10^6$, sold under the trade name CELLOSIZE HYDROXYETHYL CELLULOSE PCG-10 by the company Amerchol, or hydroxyethylcellulose with a molecular weight of 720,000, sold under the trade name NATROSOL 250 MR by the company Aqualon (Hercules).

In at least one embodiment, the hydroxyethylcellulose is present in an amount ranging from 0.01% to 5% by weight, relative to the total weight of the dye composition, such as from 0.05% to 2.5% by weight, relative to the total weight of the dye composition, and even further, for example from 0.1% to 1% by weight, relative to the total weight of the dye composition.

Fatty Substances

As indicated previously, the dye composition as disclosed herein can also comprise at least one fatty substance.

In at least one embodiment, the at least one fatty substance is chosen from non-oxyalkylenated and non-glycerolated fatty alcohols, non-oxyalkylenated and non-glycerolated fatty acid amides, carboxylic acid monoesters and polyesters, mineral oils and plant oils, and mixtures thereof.

With respect to the fatty alcohols, non-limiting mention may be made of $C_8$-$C_{30}$, for example, $C_{10}$-$C_{24}$ and further, for example, $C_{12}$-$C_{24}$ saturated or unsaturated, linear or branched alcohols, optionally containing at least one other hydroxyl group. Non-limiting examples that may be mentioned include, include oleyl alcohol, lauryl alcohol, palmityl alcohol, myristyl alcohol, behenyl alcohol, stearyl alcohol, linoleyl alcohol, linolenyl alcohol, capryl alcohol and arachidonyl alcohol, and mixtures thereof.

The fatty acid amides can be chosen, for example, from compounds derived from an alkanolamine and from a $C_8$-$C_{30}$ fatty acid. For instance, they can be chosen from amides of a $C_2$-$C_{10}$ alkanolamine and of a $C_{14}$-$C_{30}$ fatty acid, such as from amides of a $C_2$-$C_{10}$ alkanolamine and of a $C_{14}$-$C_{22}$ fatty acid.

Further, for example, the fatty acid amide can be chosen from:
- oleic acid diethanolamide, such as the amide sold under the trade name Mexanyl® GT by the company Chimex,
- myristic acid monoethanolamide, such as the amide sold under the trade name Comperlan® MM by the company Cognis, soybean fatty acid diethanolamide, such as the amide sold under the trade name Comperlan® VOD by the company Cognis, stearic acid ethanolamide, such as the amide sold under the trade name Monamid® S by the company Uniqema, oleic acid monoisopropanolamide, such as the amide sold under the trade name Witcamide® 61 by the company Witco, linoleic acid diethanolamide, such as the amide sold under the trade name Purton® SFD by the company Zschimmer Schwarz, stearic acid monoethanolamide, such as the amide sold under the trade name Monamid® 972 by the company ICI/Uniqema, behenic acid monoethanolamide, such as the amide sold under the trade name Incromide® BEM from Croda, isostearic acid monoisopropanolamide, such as the amide sold under the trade name Witcamide® SPA by the company Witco, erucic acid diethanolamide, such as the amide sold under the trade name erucic acid diethanolamide by the company Stéarineries Dubois, ricinoleic acid monoethanolamide, such as the amide sold under the trade name ricinoleic monoethanolamide by the company Stéarineries Dubois.

With respect to the linear or branched, saturated or unsaturated carboxylic acid monoesters or polyesters, they may comprise, for example at least one $C_8$-$C_{30}$, for instance a $C_{10}$-$C_{24}$ and further, a $C_{12}$-$C_{24}$ hydrocarbon-based chain, originating from the acid or alcohol part, and at least one $C_1$-$C_8$ and for example a $C_1$-$C_6$ chain. Furthermore, if the carboxylic acid comprises several carboxylic functional groups, they may, for example, all be esterified. Finally, it should be noted that the alcohols can, in at least one embodiment, be monofunctional alcohols.

Non-limiting examples that may be mentioned include but are not limited to the esters of oleic acid, lauric acid, palmitic acid, myristic acid, behenic acid, stearic acid, linolenic acid, linolenic acid, capric acid or arachidonic acid, and mixtures thereof, such as, for example, oleopalmitic, oleostearic, palmitostearic, etc. mixtures.

Further non-limiting mention may be made of the isopropyl diester of sebacic acid (diisopropyl sebacate), dioctyl adipate and dicaprylyl maleate.

In at least one embodiment, the esters can be chosen from those obtained from $C_{12}$-$C_{24}$ acids, for example those comprising a carboxylic group, and from a saturated, linear or branched $C_3$-$C_6$ monoalcohol.

According to this embodiment of the present disclosure, the ester can be chosen from isopropyl palmitate and isopropyl myristate, alone or as mixtures.

Liquid paraffin is an example of a mineral oil that may be used as fatty substance in the composition.

In at least one embodiment the plant oils include but are not limited to avocado oil, olive oil and liquid jojoba wax.

In at least one embodiment, the fatty substance is chosen from non-oxyalkylenated and non-glycerolated fatty alcohols.

According to at least one embodiment as disclosed herein, the dye composition comprises a total content of not more than 10%, such as from 1% to 9%, of the at least one fatty substance by weight relative to the total weight of the dye composition.

In accordance with the present disclosure, the weight ratio of the total amount of the at least one surfactant chosen from nonionic surfactants to the amount of the at least one fatty substance is greater than 1.75, for instance greater than 2 and further, for example, greater than 3.

The weight ratio of the total amount of the at least one surfactant chosen from nonionic surfactants and anionic surfactants to the total amount of the at least one fatty substance is, for example, less than 20, such as less than 15 and further still, for example, less than 10.

Cationic Associative Polymers

As indicated previously, the composition according to the present disclosure comprises at least one cationic associative polymer.

The chemical structure of the associative polymers can be identified by the presence of hydrophilic regions that ensure solubility in water, and hydrophobic regions via which the polymers, in an aqueous medium, assemble with each other or with the hydrophobic parts of other molecules. Such polymers can, in an aqueous medium, reversibly associate with each other or with other molecules.

The associative polymers used in the context of the present disclosure include but are not limited to amphiphilic polymers comprising at least one fatty chain.

For the purposes of the present disclosure, the term "polymer" is understood to mean compounds having in their structure a repetition of at least one sequence other than the ethylene oxide or propylene oxide or glycerol sequence if this type of sequence is present.

For instance, the cationic associative polymer present in the composition according to the present disclosure can be chosen from quaternized cellulose derivatives, cationic polyurethanes, cationic polyvinyllactams and cationic acrylic terpolymers; these compounds comprising at least one fatty chain.

Quaternized Cellulose Derivatives

These polymers can be chosen from, for example:

quaternized celluloses modified with groups comprising at least one fatty chain, such as alkyl, arylalkyl or alkylaryl groups, for example comprising at least 8 carbon atoms, and mixtures thereof; and quaternized hydroxyethylcelluloses modified with groups comprising at least one fatty chain, such as alkyl, arylalkyl or alkylaryl groups, for example comprising at least 8 carbon atoms, and mixtures thereof.

The alkyl radicals borne by the above quaternized celluloses or hydroxyethylcelluloses may contain, for example, from 8 to 30 carbon atoms. For instance, the aryl radicals can be phenyl, benzyl, naphthyl or anthryl groups.

Examples of quaternized alkylhydroxyethylcelluloses comprising $C_8$-$C_{30}$ fatty chains include but are not limited to the products QUATRISOFT LM 200, QUATRISOFT LM-X 529-18-A, QUATRISOFT LM-X 529-18B ($C_{12}$ alkyl) and QUATRISOFT LM-X 529-8 ($C_{18}$ alkyl) sold by the company Amerchol, and the products CRODACEL QM, CRODACEL QL ($C_{12}$ alkyl) and CRODACEL QS ($C_{18}$ alkyl) sold by the company Croda.

Cationic Polyurethanes

According to at least one embodiment of the present disclosure, the cationic associative polyurethanes that are suitable correspond to the formula (Ia) below:

$$R\text{—}X\text{—}(P)_n\text{-}[L\text{-}(Y)_m]_r\text{-}L'\text{-}(P')_p\text{—}X'\text{—}R' \qquad (Ia)$$

in which:

R and R', which may be identical or different, are chosen from hydrophobic groups and hydrogen atoms;

X and X', which may be identical or different, are chosen from groups comprising an amine function optionally bearing a hydrophobic group, or alternatively a group L";

L, L' and L", which may be identical or different, are chosen from groups derived from diisocyanates;

P and P', which may be identical or different, are chosen from groups comprising an amine function optionally bearing a hydrophobic group;

Y is a hydrophilic group;

r is an integer from 1 to 100, such as from 1 to 50 and further, for example from 1 to 25;

n, m and p each range, independently of each other, from 0 to 1,000; the molecule containing at least one protonated or quaternized amine function and at least one hydrophobic group.

These compounds have been described, for example, in European Patent Application No. EP 1 174 450.

According to at least one embodiment of the present disclosure, the only hydrophobic groups are the groups R and R' at the chain ends.

As disclosed herein, one example of a family of cationic amphiphilic polyurethanes is the one corresponding to formula (Ia) described above and in which:

R and R' are both independently chosen from hydrophobic groups,

X and X' each are a group L", n and p range from 1 to 1000, and

L, L', L", P, P', Y and m have the same meaning provided above.

Another family of cationic amphiphilic polyurethanes, for example, includes the one corresponding to formula (Ia) above in which:

R and R' are both independently chosen from hydrophobic groups,

X and X' each are a group L", n and p are 0, and

L, L', L", Y and m have the same meaning provided above.

The fact that n and p are 0 is understood to mean that these polymers do not comprise units derived from a monomer containing an amine function, incorporated into the polymer during the polycondensation. The protonated amine functions of these polyurethanes result from the hydrolysis of excess isocyanate functions, at the chain end, followed by alkylation of the primary amine functions formed with alkylating agents containing a hydrophobic group, i.e. compounds of the type RQ or R'Q, in which R and R' are as defined above and Q is a leaving group such as a halide, a sulfate, etc.

Yet another example of a family of cationic amphiphilic polyurethanes is the one corresponding to formula (Ia) above in which:

R and R' are both independently chosen from hydrophobic groups,

X and X' are both independently chosen from groups comprising a quaternary amine, n and p are zero, and L, L', Y and m have the same meaning provided above.

The number-average molecular mass of the cationic amphiphilic polyurethanes can range, for example, from 400 to 500,000, such as from 1000 to 400,000 and further, for example, from 1000 to 300,000.

As used herein, the expression "hydrophobic group" is understood to mean a radical or polymer containing a saturated or unsaturated, linear or branched hydrocarbon-based chain, which may comprise one or more hetero atoms such as P, O, N or S, or a radical containing a perfluoro or silicone chain. When the hydrophobic group is a hydrocarbon-based radical, it comprises at least 10 carbon atoms, for example from 10 to 30 carbon atoms, such as from 12 to 30 carbon atoms and even further still, for example, from 18 to 30 carbon atoms.

According to the present disclosure, the hydrocarbon-based group can be derived from a monofunctional compound.

By way of a non-limiting example, the hydrophobic group may be derived from a fatty alcohol such as stearyl alcohol, dodecyl alcohol or decyl alcohol. It may also be a hydrocarbon-based polymer, for instance polybutadiene.

When X and/or X' is a group comprising a tertiary or quaternary amine, X and/or X' may represent one of the following formulae:

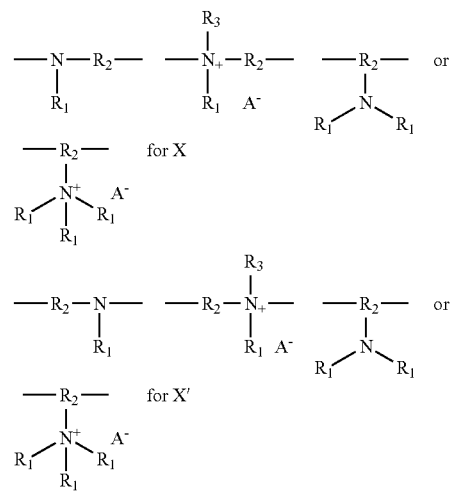

in which:

$R_2$ is a linear or branched alkylene radical comprising from 1 to 20 carbon atoms, optionally comprising a saturated or unsaturated ring, or an arylene radical, wherein at least one of the carbon atoms can be possibly replaced with a hetero atom chosen from N, S, O and P;

$R_1$ and $R_3$, which may be identical or different, are a linear or branched $C_1$-$C_{30}$ alkyl or alkenyl radical or an aryl radical, wherein at least one of the carbon atoms can be possibly replaced with a hetero atom chosen from N, S, O and P;

$A^-$ is a physiologically acceptable counter-ion.

The groups L, L' and L" represent a group of formula:

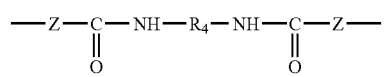

in which:

Z is —O—, —S— or —NH—; and $R_4$ is a linear or branched alkylene radical comprising from 1 to 20 carbon atoms, optionally comprising a saturated or unsaturated ring, or an arylene radical, wherein at least one of the carbon atoms can be possibly replaced with a hetero atom chosen from N, S, O and P.

The groups P and P' comprising an amine function may be chosen from at least one of the following formulae:

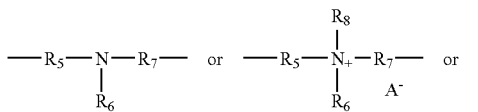

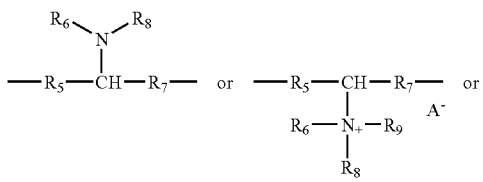

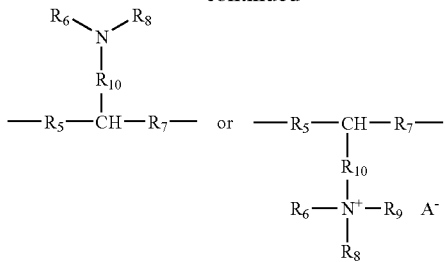

-continued in which:

$R_5$ and $R_7$ have the same meanings as $R_2$ defined above;

$R_6$, $R_8$ and $R_9$ have the same meanings as $R_1$ and $R_3$ defined above;

$R_{10}$ is a linear or branched, optionally unsaturated alkylene group possibly containing at least one hetero atom chosen from N, O, S and P; and $A^-$ is a physiologically acceptable counter-ion.

With respect to Y, as used herein, the term "hydrophilic group" is understood to mean a polymeric or nonpolymeric water-soluble group.

By way of example, when the hydrophilic group is not a polymer, non-limiting mention may be made of ethylene glycol, diethylene glycol and propylene glycol.

However, when it is a hydrophilic polymer, in accordance with at least one embodiment of the present disclosure, non-limiting mention may be made, for example, of polyethers, sulfonated polyesters, sulfonated polyamides and a mixture of these polymers. The hydrophilic compound can be a polyether, for example, such as a poly(ethylene oxide) or poly(propylene oxide).

The hydrophilic group noted Y in formula (Ia) is optional. For example, the units containing a protonated or quaternary amine function may suffice to provide the solubility or the water-dispersibility required for this type of polymer in an aqueous solution.

Although the presence of a hydrophilic group Y is optional, cationic amphiphilic polyurethanes comprising such a group are used in at least one embodiment.

The cationic amphiphilic polyurethanes can be water-soluble or water-dispersible.

Cationic Polyvinyllactams

The associative cationic poly(vinyllactam) polymers that may be used in the context of the present disclosure comprise:
a) at least one monomer of vinyllactam or alkylvinyllactam type;
b) at least one monomer of structure (Ib) or (IIb) below:

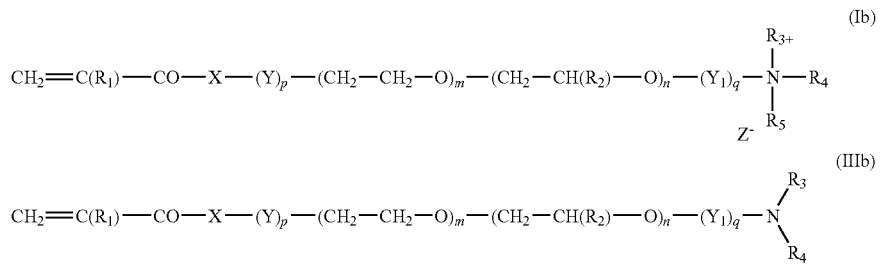

in which:

X is chosen from an oxygen atom and a radical $NR_6$, $R_1$ and $R_6$ are, independently of each other, chosen from hydrogen atoms and linear or branched $C_1$-$C_5$ alkyl radicals, $R_2$ is a linear or branched $C_1$-$C_4$ alkyl radical, $R_3$, $R_4$ and $R_5$ are, independently of each other, chosen from hydrogen atoms, linear or branched $C_1$-$C_{30}$ alkyl radicals, and radicals of formula (IIIb):

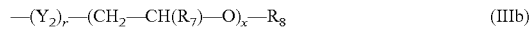

Y, $Y_1$ and $Y_2$ are, independently of each other, chosen from linear or branched $C_2$-$C_{16}$ alkylene radicals, $R_7$ is chosen from a hydrogen atom, a linear or branched $C_1$-$C_4$ alkyl radical, and a linear or branched $C_1$-$C_4$ hydroxyalkyl radical, $R_8$ is chosen from a hydrogen atom and a linear or branched $C_1$-$C_{30}$ alkyl radical, p, q and r are, independently of each other, either the value 0 or the value 1, m and n are, independently of each other, an integer ranging from 0 to 100, x is an integer ranging from 1 to 100, Z is an organic or mineral acid anion, with the proviso that:

at least one of the substituents $R_3$, $R_4$, $R_5$ or $R_8$ is a linear or branched $C_8$-$C_{30}$, for example, such as a $C_9$-$C_{30}$ alkyl radical, if m or n is an integer other than zero, then q is equal to 1, if m or n is an integer equal to zero, then p or q is equal to 0.

The associative cationic poly(vinyllactam) polymers that may be used according to the present disclosure may be crosslinked or noncrosslinked and may also be block polymers.

For example, the counterion $Z^-$ of the monomers of formula (Ib) can be chosen from halide ions, phosphate ions, the methosulfate ion and the tosylate ion.

According to at least one embodiment of the present disclosure, $R_3$, $R_4$ and $R_5$ are, independently of each other, chosen from hydrogen atoms and linear or branched $C_1$-$C_{30}$ alkyl radicals.

For instance, the monomer b) is a monomer of formula (Ib) for which, for example, m and n are equal to 0.

The vinyllactam or alkylvinyllactam monomer can be, for example, a compound of structure (IVb):

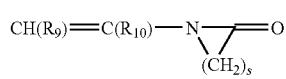 (IVb)

in which:

s is an integer ranging from 3 to 6, $R_9$ is chosen from a hydrogen atom and a $C_1$-$C_5$ alkyl radical, $R_{10}$ is chosen from a hydrogen atom and a $C_1$-$C_5$ alkyl radical, with the proviso that at least one of the radicals $R_9$ and $R_{10}$ is a hydrogen atom.

According to at least one embodiment, the monomer (IVb), as disclosed herein, is vinylpyrrolidone.

The cationic poly(vinyllactam) polymers may also comprise at least one additional monomer, for example cationic or nonionic monomers.

According to the present disclosure, non-limiting mention may be made of the following terpolymers comprising at least:

a) one monomer of formula (IVb), b) one monomer of formula (Ib) in which p=1, q=0, $R_3$ and $R_4$, independently of each other, are chosen from a hydrogen atom and a $C_1$-$C_5$ alkyl radical and $R_5$ is a $C_8$-$C_{24}$, for example a $C_9$-$C_{24}$ alkyl radical, and c) one monomer of formula (IIb) in which $R_3$ and $R_4$ are, independently of each other, chosen from a hydrogen atom and a $C_1$-$C_5$ alkyl radical.

In at least one embodiment, terpolymers comprising, by weight, 40% to 95% of monomer (a), 0.1% to 55% of monomer (c) and 0.25% to 50% of monomer (b) are used.

Such polymers are described in Patent Application No. WO 00/68282, the content of which is incorporated by reference herein.

As cationic poly(vinyllactam) polymers according to the present disclosure, vinylpyrrolidone/dimethylaminopropylmethacrylamide/dodecyldimethylmethacryl-amidopropylammonium tosylate terpolymers, vinylpyrrolidone/dimethylamino-propylmethacrylamide/cocoyidimethylmethacrylamidopropylammonium tosylate terpolymers, vinylpyrrolidone/dimethylaminopropylmethacrylamide/lauryldimethylmeth-acrylamidopropylammonium tosylate or chloride terpolymers can be used, for example.

The weight-average molecular mass of the cationic associative poly(vinyllactam) polymers according to the present disclosure may range from 500 to $20 \times 10^6$. For example, the weight-average molecular mass may range from 200,000 to $2 \times 10^6$ and even further still, for example, from 400,000 to 800,000.

Acrylic Terpolymers

Among these polymers, non-limiting mention may be made of acrylic terpolymers comprising:

from 5% to 80% by weight, for example from 15% to 70% by weight and even further, for example, from 40% to 70% by weight of an acrylate monomer (a) chosen from a $C_1$-$C_6$ alkyl acrylate and a $C_1$-$C_6$ alkyl methacrylate;

from 5% to 80% by weight, such as from 10% to 70% by weight and even further from 20% to 60% by weight, of a monomer (b) chosen from a heterocyclic vinyl compound comprising at least one nitrogen or sulfur atom, a (meth)acrylamide, a mono- or di($C_1$-$C_4$)alkylamino($C_1$-$C_4$)alkyl (meth)acrylate and a mono- or di($C_1$-$C_4$)alkylamino($C_1$-$C_4$)alkyl(meth)acrylamide;

from 0.1% to 30% by weight, such as from 0.1% to 10% by weight, of a monomer (c) chosen from: (i) a urethane produced by reaction between a monoethylenic unsaturated isocyanate and a nonionic surfactant with a $C_1$-$C_4$ alkoxy end; (ii) a block copolymer of 1,2-butylene oxide and of 1,2-ethylene oxide; (iii) a copolymerizable ethylenic unsaturated surfactant monomer obtained by condensation of a nonionic surfactant with an α,β-ethylenic unsaturated carboxylic acid or its anhydride; (iv) a surfactant monomer chosen from the products of reaction such as a urea of a monoethylenic unsaturated monoisocyanate with a nonionic surfactant containing an amine functional group; (v) a (meth)allyl ether of formula $CH_2=CR_1CH_2OA_mB_nA_pR_2$ in which $R_1$ is a hydrogen atom or a methyl group; A is a propyleneoxy or butyleneoxy group; B is ethyleneoxy; n is equal to zero or an integer less than or equal to 200, for example less than 100; m and p are zero or an integer less than n; $R_2$ is a hydrophobic group of at least 8 carbon atoms, for example $C_8$-$C_{30}$; and (vi) a nonionic monomer of urethane type produced by reaction of a monohydric nonionic surfactant with a monoethylenic unsaturated isocyanate; the weight percentages of monomers being based on the total weight of the monomers constituting the terpolymer.

Acrylate monomers (a) that may be used, for example, comprise $C_2$-$C_6$ alkyl acrylates. For instance, ethyl acrylate can be used.

Non-limiting examples of monomers (b) which can be mentioned include but are not limited to N,N-dimethylaminoethyl methacrylate (DMAEMA), N,N-diethylaminoethyl acrylate, N,N-diethylaminoethyl methacrylate, N-t-butylaminoethyl acrylate, N-t-butylaminoethyl methacrylate, N,N-dimethylamino-propylacrylamide, N,N-dimethylaminopropylmethacrylamide, N,N-diethylaminopropylacrylamide and N,N-di-ethylaminopropylmethacrylamide. For example, N,N-dimethylaminoethyl methacrylate can be used.

The monomers (c) include but are not limited to the copolymerizable ethylenic unsaturated surfactant monomers obtained by condensing a nonionic surfactant with an α,β-ethylenic unsaturated carboxylic acid or its anhydride, for instance $C_3$-$C_4$ mono- or dicarboxylic acids or their anhydrides, for example acrylic acid, methacrylic acid, crotonic acid, maleic acid, maleic anhydride and most particularly itaconic acid and itaconic anhydride.

For instance, the monomers (c) that may be used correspond to the copolymerizable ethylenic unsaturated surfactant monomers obtained by condensing a nonionic surfactant with itaconic acid. Among the nonionic surfactants which may be used, non-limiting mention may be made of $C_{10}$-$C_{30}$ fatty alcohols alkoxylated with 2 to 100 mol, for example, from 5 to 50 mol of an alkylene oxide, for instance polyethylene glycol ethers of $C_{10}$-$C_{30}$ fatty alcohols and further, for example the polyethylene glycol ethers of cetyl alcohol which are known as Ceteth in the CTFA Dictionary, 7th Edition, 1997.

Conventional methods for preparing these acrylic terpolymers are known to those skilled in the art. Such methods include solution polymerization, precipitation polymerization and emulsion polymerization. Terpolymers in accordance with the present disclosure and methods for preparing them are described in European Patent Application Nos. EP-A-0 824 914 and EP-A-0 825 200.

Among these terpolymers, non-limiting examples include the "Structure® Plus" polymer sold by the company National Starch, which comprises acrylates, amino (meth)acrylates and $C_{10}$-$C_{30}$ alkyl itaconate, polyoxyethylenated with 20 mol of ethylene oxide, in the form of an aqueous dispersion containing 20% Active Material.

In addition to these monomers, the terpolymers can comprise other monomers that allow the terpolymers to be crosslinked. These monomers may be used in relatively low proportions, of up to 2% by weight, relative to the total weight of the monomers used to prepare the terpolymers. Such crosslinking monomers may comprise aromatic monomers bearing several vinyl substituents, alicyclic monomers bearing several vinyl substituents, bifunctional esters of phthalic acid, bifunctional esters of methacrylic acid, multifunctional esters of acrylic acid, N-methylenebisacrylamide and aliphatic monomers bearing several vinyl substituents such as dienes, trienes and tetraenes.

Crosslinking monomers may include, for example, divinylbenzenes, trivinylbenzenes, 1,2,4-trivinylcyclohexene, 1,5-hexadiene, 1,5,9-decatriene, 1,9-decadiene, 1,5-heptadiene, diallyl phthalates, ethylene glycol dimethacrylate, polyethylene glycol dimethacrylates, penta- and tetraacrylates, triallyl pentaerythritols, octaallyl sucroses, cycloparaffins, cycloolefins and N-methylenebisacrylamide.

In the present disclosure, the at least one cationic associative polymer can be used in an amount that ranges from 0.01% to 5% by weight, relative to the total weight of the dye composition. This amount can range from 0.05% to 2.5% by weight, relative to the total weight of the dye composition. In accordance with at least one embodiment of the present disclosure, the at least one cationic associative polymer may be present in an amount ranging from 0.1% to 1% by weight, relative to the total weight of the dye composition.

Dyes

The composition according to the present disclosure also comprises at least one dye chosen from oxidation dye precursors and direct dyes.

The at least one oxidation dye precursor can be chosen from oxidation bases and couplers.

The oxidation bases can be chosen from the oxidation bases conventionally used for oxidation dyeing, among which non-limiting mention may be made, for example, of para-phenylenediamines, bis(phenyl)alkylenediamines, para-aminophenols, ortho-aminophenols and heterocyclic bases, and the addition salts thereof with an acid or with an alkaline agent.

The para-phenylenediamines that may be mentioned include but are not limited to, for example, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxy-ethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediam ine, 2-β-hydroxyethyloxy-para-phenylenediamine, 2-α-acetylaminoethyloxy-para-phenylenediamine, N-(β-methoxyethyl)-para-phenylenediamine and 4'-aminophenyl-1-(3-hydroxy)pyrrolidine, and the addition salts thereof with an acid or with an alkaline agent.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid or with an alkaline agent, may be used, for example.

The bis(phenyl)alkylenediamines that may be used include but are not limited to, for example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the addition salts thereof with an acid or with an alkaline agent.

The para-aminophenols that may be used include but are not limited to, for example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid or with an alkaline agent.

The ortho-aminophenols that may be used, include but are not limited to, for example, 2-aminophenol, 2-amino-5-methylphenol, 2-amino-6-methylphenol and 5-acetamido-2-aminophenol, and the addition salts thereof with an acid or with an alkaline agent.

The heterocyclic bases that may be used, include but are not limited to, for example, pyridine derivatives such as 2,3-diamino-6-methoxypyridine; pyrimidine derivatives such as 2,4,5,6-tetraminopyrimidine or 4-hydroxy-2,5,6-triaminopyrimidine; and pyrazole derivatives such as 1N-β-hydroxyethyl-4,5-diaminopyrazole; and the addition salts thereof with an acid or with an alkaline agent.

When they are used, the oxidation base(s) may be present(s) in an amount ranging from 0.0005% to 12% by weight, relative to the total weight of the dye composition, for example ranging from 0.005% to 6% by weight, relative to the total weight of the dye composition.

The dye composition may also comprise, together with said at least one oxidation base, at least one coupler so as to modify or to enrich with tints the shades obtained.

The coupler(s) that may be used may be chosen from the couplers conventionally used in oxidation dyeing, and among which non-limiting mention may be made for instance of meta-phenylenediamines, meta-aminophenols, meta-diphenols and heterocyclic couplers, and the addition salts thereof, with an acid or with an alkaline agent.

These couplers may be chosen from 2-methyl-5-aminophenol, 5-N-(β-hydroxyethyl)amino-2-methylphenol, 3-aminophenol, 2-methyl-5-amino-6-chlorophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxy-ethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2-amino-3-hydroxypyridine, 2,6-dihydroxy-4-methylpyridine, 1H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methyl-pyrazolo[1,5-a]benzimidazole, and the addition salts thereof with an acid or with an alkaline agent.

When they are present, the at least one coupler may be present in an amount ranging from 0.0001% to 15% by weight, such as from 0.005% to 12% by weight, relative to the total weight of the dye composition. In accordance with at least one embodiment, for example, the at least one coupler may be present in an amount ranging from 0.01% to 10% by weight, relative to the total weight of the dye composition.

In general, the addition salts with an acid can be chosen, for example, from the hydrochlorides, hydrobromides, sulfates, citrates, succinates, tartrates, tosylates, benzenesulfonates, lactates and acetates.

With respect to the direct dye, it may be of nonionic, cationic or anionic nature.

Non-limiting examples that may be mentioned include nitrobenzene dyes, azo, azomethine, methine, tetraazapentamethine, anthraquinone, naphthoquinone, benzoquinone, phenothiazine, indigoid, xanthene, phenanthridine, phthalocyanin and triarylmethane-based dyes and natural dyes, alone and as mixtures.

The at least one direct dye may also be chosen, for example, from the following red or orange nitrobenzene dyes:
1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
1-amino-2-nitro-4-(β-hydroxyethyl)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy)benzene,
1-(β,γ-dihydroxypropyl)oxy-3-nitro-4-(β-hydroxyethyl)aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine, and
1-amino-2-nitro-4-hydroxy-5-methylbenzene.

The at least one direct dye may also be chosen from yellow and green-yellow nitrobenzene direct dyes; where non-limiting mention may be made, for example, of the compounds chosen from:

1-β-hydroxyethyloxy-3-methylamino-4-nitrobenzene,
1-methylamino-2-nitro-5-(β,γ-dihydroxypropyl)oxybenzene,
1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulfonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene, and
4-(β-hydroxyethyl)amino-3-nitrobenzamide.

Non-limiting mention may also be made of blue or violet nitrobenzene direct dyes, for instance:
1-(β-hydroxyethyl)amino-4-N,N-bis(β-hydroxyethyl)amino-2-nitrobenzene,
1-(γ-hydroxypropyl)amino-4,N,N-bis(β-hydroxyethyl)amino-2-nitrobenzene,
1-(β-hydroxyethyl)amino-4-(N-methyl-N-β-hydroxyethyl)amino-2-nitrobenzene,
1-(β-hydroxyethyl)amino-4-(N-ethyl-N-α-hydroxyethyl)amino-2-nitrobenzene,
1-(β,γ-dihydroxypropyl)amino-4-(N-ethyl-N-β-hydroxyethyl)amino-2-nitrobenzene,
2-nitro-para-phenylenediamines having the following formula:

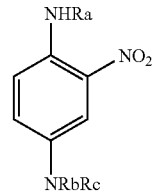

in which:
Rb is chosen from a $C_1$-$C_4$ alkyl radical, a β-hydroxyethyl radical, a β-hydroxypropyl radical, and a γ-hydroxypropyl radical;
Ra and Rc, which may be identical or different, are chosen from β-hydroxyethyl, β-hydroxypropyl, γ-hydroxypropyl and β,γ-dihydroxypropyl radicals, wherein at least one of the radicals Rb, Rc or Ra is a γ-hydroxypropyl radical with the proviso that Ra and Rc are not simultaneously a β-hydroxyethyl radical when Rb is a γ-hydroxypropyl radical, such as those described in French Patent No. FR 2 692 572.

Among the azo direct dyes that may be used according to the present disclosure, non-limiting mention may be made of the cationic azo dyes described in patent applications WO 95/15144, WO 95/01772, EP 714 954, FR 2 822 696, FR 2 825 702, FR 2 825 625, FR 2 822 698, FR 2 822 693, FR 2 822 694, FR 2 829 926, FR 2 807 650, WO 02/078 660, WO 02/100 834, WO 02/100 369 and FR 2 844 269.

Among these compounds, non-limiting mention may be made of the following dyes, for example:
- 1,3-dimethyl-2-[[4-(dimethylamino)phenyl]azo]-1H-imidazolium chloride,
- 1,3-dimethyl-2-[(4-aminophenyl)azo]-1H-imidazolium chloride, and
- 1-methyl-4-[(methylphenylhydrazono)methyl]pyridinium methyl sulfate.

The azo direct dyes that may be mentioned include but are not limited to the following dyes as described in the Colour Index International 3rd Edition: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, and Disperse Black 9.

Non-limiting mention may also be made of 1-(4'-aminodiphenylazo)-2-methyl-4-[bis(β-hydroxyethyl)amino]benzene and 4-hydroxy-3-(2-methoxyphenylazo)-1-naphthalenesulfonic acid.

Non-limiting examples of the quinone direct dyes that may be used, include but are not limited to: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds:
- 1-N-methylmorpholiniumpropylamino-4-hydroxyanthraquinone;
- 1-aminopropylamino-4-methylaminoanthraquinone;
- 1-aminopropylaminoanthraquinone;
- 5-β-hydroxyethyl-1,4-diaminoanthraquinone;
- 2-aminoethylaminoanthraquinone; and
- 1,4-bis(β,γ-dihydroxypropylamino)anthraquinone.

By way of example, the azine dyes that may be used include but are not limited to: Basic Blue 17, and Basic Red 2.

Further, among the cationic methine direct dyes that may be used, non-limiting mention may be made of Basic Red 14, Basic Yellow 13, and Basic Yellow 29.

Among the triarylmethane dyes that may be used according to the present disclosure, non-limiting mention may be made of the following compounds: Basic Green 1, Acid Blue 9, Basic Violet 3, Basic Violet 14, Basic Blue 7, Acid Violet 49, Basic Blue 26, and Acid Blue 7.

The indoamine dyes that may be used according to the present disclosure, include but are not limited to:
- 2-β-hydroxyethylamino-5-[bis(β-4'-hydroxyethyl)amino]anilino-1,4-benzoquinone;
- 2-β-hydroxyethylamino-5-(2'-methoxy-4'-amino)anilino-1,4-benzoquinone;
- 3-N(2'-chloro-4'-hydroxy)phenylacetylamino-6-methoxy-1,4-benzoquinoneimine;
- 3-N(3'-chloro-4'-methylamino)phenylureido-6-methyl-1,4-benzoquinoneimine; and
- 3-[4'-N-(ethylcarbamylmethyl)amino]phenylureido-6-methyl-1,4-benzoquinoneimine.

The dye composition may also comprise natural direct dyes, for instance lawsone, juglone, alizarin, purpurin, carminic acid, kermesic acid, purpurogallin, protocatechaldehyde, indigo, isatin, curcumin, spinulosin or apigenidin. Extracts or decoctions comprising these natural dyes, for example henna-based poultices or extracts, may also be used.

The amount of direct dyes, when they are present, ranges from 0.0005% to 15% by weight, relative to the total weight of the dye composition, and further for example from 0.005% to 12% by weight, relative to the total weight of the dye composition. According to at least one embodiment of the present disclosure, the amount of the at least one direct dye can be present in an amount ranging from 0.01% to 5% by weight, relative to the total weight of the dye composition.

Basifying Agents

The composition according to the present disclosure may also comprise at least one basifying agent.

The basifying agents that may be mentioned, for example, include but are not limited to aqueous ammonia, alkali metal carbonates, $C_2$-$C_{10}$ alkanolamines such as monoethanolamine, diethanolamine and triethanolamine and also derivatives thereof, oxyethylenated and/or oxypropylenated hydroxyalkylamines and ethylenediamines, sodium hydroxide, potassium hydroxide, alkali metal or alkaline-earth metal silicates and the compounds having the following formula:

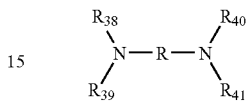

in which R is a propylene residue optionally substituted with a hydroxyl group or a $C_1$-$C_4$ alkyl radical; $R_{38}$, $R_{39}$, $R_{40}$ and $R_{41}$, which may be identical or different, are chosen from hydrogen atoms, $C_1$-$C_4$ alkyl radicals, and $C_1$-$C_4$ hydroxyalkyl radicals.

For instance, the at least one basifying agent can be chosen from aqueous ammonia, alkanolamines and combinations of alkanolamines with alkali metal or alkaline-earth metal silicates.

According to at least one embodiment of the present disclosure, for example, the composition does not comprise aqueous ammonia as the at least one basifying agent.

It should moreover be noted that the pH may also be adjusted by using acidifying agents, for instance mineral or organic acids such as hydrochloric acid, orthophosphoric acid or sulfuric acid, carboxylic acids, for instance acetic acid, tartaric acid, citric acid or lactic acid, or sulfonic acids.

For example, the amount of basifying and/or acidifying agent is such that the pH of the dye composition ranges from 3 to 12, such as from 4 to 11 and further still from 7 to 11.

Cationic and Amphoteric Substantive Polymers

The composition according to the present disclosure may also comprise at least one substantive polymer chosen from cationic substantive polymers andr amphoteric substantive polymers.

It should be noted that, for the purposes of the present disclosure, the term "cationic polymer" is understood to mean any polymer containing cationic groups and/or groups that may be ionized into cationic groups.

Such polymers may be chosen from those already known per se as improving the cosmetic properties of the hair, for example, those described in European Patent Application No. EP-A-337 354 and in French Patent Nos. FR-2 270 846, 2 383 660, 2 598 611, 2 470 596 and 2 519 863.

According to the present disclosure, the cationic polymers that can be used may be chosen from those containing units comprising primary, secondary, tertiary and/or quaternary amine groups, which may either form part of the main polymer chain or may be borne by a side substituent directly attached thereto.

The cationic polymers used generally have a number-average molecular mass ranging from 500 to $5 \times 10^6$ approximately, and further for example, ranging from $10^3$ to $3 \times 10^6$ approximately.

Among the cationic polymers that may be mentioned, non-limiting examples include polyamine, polyamino amide and polyquaternary ammonium polymers.

These are known products and are described, for example, in French Patents Nos. 2 505 348 and 2 542 997. Among these polymers, non-limiting mention may be made of:

(1) homopolymers or copolymers derived from acrylic or methacrylic esters or amides and comprising at least one of the units of formula (I), (II), (III) or (IV) below:

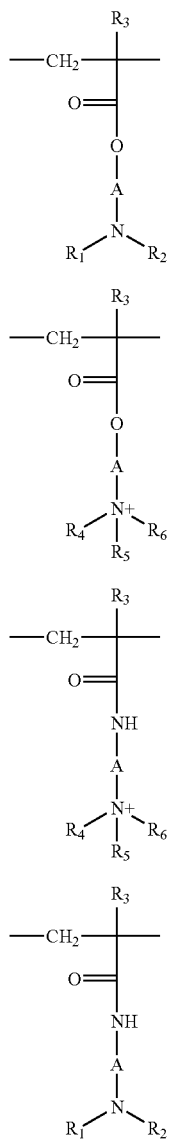

in which:

$R_3$, which may be identical or different, is chosen from a hydrogen atom and a $CH_3$ radical;

A, which may be identical or different, is chosen from a linear or branched alkyl group of 1 to 6 carbon atoms, for example, 2 or 3 carbon atoms, and from a hydroxyalkyl group of 1 to 4 carbon atoms;

$R_4$, $R_5$ and $R_6$, which may be identical or different, are an alkyl group comprising from 1 to 18 carbon atoms or a benzyl radical, for example an alkyl group comprising from 1 to 6 carbon atoms;

$R_1$ and $R_2$, which may be identical or different, are chosen from hydrogen and an alkyl group comprising from 1 to 6 carbon atoms, such as a methyl or ethyl group;

X is an anion derived from an inorganic or organic acid, such as a methosulfate anion or a halide such as chloride or bromide.

For example, the polymers of family (1) can also comprise one or more units derived from comonomers which may be chosen from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinylcaprolactam, and vinyl esters.

Thus, among these polymers of family (1), non-limiting mention may be made of:

copolymers of acrylamide and of dimethylaminoethyl methacrylate quaternized with dimethyl sulfate or with a dimethyl halide, such as the product sold under the name HERCOFLOC by the company Hercules;

the copolymers of acrylamide and of methacryloyloxyethyltrimethylammonium chloride described, for example, in European Patent Application No. EP-A-080 976 and sold under the name BINA QUAT P 100 by the company Ciba Geigy;

the copolymer of acrylamide and of methacryloyloxyethyltrimethylammonium methosulfate sold under the name RETEN by the company Hercules;

quaternized or non-quaternized vinylpyrrolidone/dialkylaminoalkyl acrylate or methacrylate copolymers, such as the products sold under the name "Gafquat" by the company ISP, for instance "Gafquat 734" or "Gafquat 755", or alternatively the products known as "Copolymer 845, 958 and 937". These polymers are described in detail in French Patent Nos. 2 077 143 and 2 393 573;

dimethylaminoethyl methacrylate/vinylcaprolactam/vinylpyrrolidone terpolymers, such as the product sold under the name GAFFIX VC 713 by the company ISP; and vinylpyrrolidone/methacrylamidopropyldimethylamine copolymers sold for example under the name STYLEZE CC 10 by ISP, and quaternized vinylpyrrolidone/dimethylaminopropyl methacrylamide copolymers such as the product sold under the name "Gafquat HS 100" by the company ISP.

(2) The cellulose ether derivatives comprising quaternary ammonium groups, which are described in French Patent No. 1 492 597, such as the polymers sold under the names "JR" (JR 400, JR 125, JR 30M) or "LR" (LR 400, LR 30M) by the company Union Carbide Corporation. These polymers are also defined in the CTFA Dictionary as hydroxyethylcellulose quaternary ammoniums that have reacted with an epoxide substituted with a trimethylammonium group.

(3) Cationic cellulose derivatives such as the copolymers of cellulose or cellulose derivatives grafted with a water-soluble quaternary ammonium monomer, described, for example, in U.S. Pat. No. 4,131,576, such as hydroxyalkylcelluloses, for instance hydroxymethyl-, hydroxyethyl- or hydroxypropylcelluloses grafted for instance with a methacryloylethyltrimethylammonium, methacrylamidopropyltrimethylammonium or dimethyldiallylammonium salt.

The commercial products corresponding to this definition include, for example, the products sold under the name CELQUAT L 200 and CELQUAT H 100 by the company National Starch.

(4) The cationic guar gums described, for example, in U.S. Pat. Nos. 3,589,578 and 4,031,307, such as guar gums containing trialkylammonium cationic groups. Use is made, for example, of guar gums modified with a salt (e.g. chloride) of 2,3-epoxypropyltrimethyl-ammonium.

For example, such products are sold under the trade names JAGUAR C13S, JAGUAR C15, JAGUAR C17 and JAGUAR C162 by the company Meyhall.

(5) Polymers consisting of piperazinyl units and of divalent alkylene or hydroxyalkylene radicals containing straight or branched chains, optionally interrupted by oxygen, sulfur or nitrogen atoms or by aromatic or heterocyclic rings, and also the oxidation and/or quaternization products of these polymers. Such polymers are described, for example, in French Patent Nos. 2 162 025 and 2 280 361.

(6) Water-soluble polyamino amides prepared for instance by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they contain one or more tertiary amine functions, they can be quaternized. Such polymers are described, for example, in French Patent No. 2 252 840 and 2 368 508.

(7) The polyamino amide derivatives resulting from the condensation of polyalkylene polyamines with polycarboxylic acids followed by alkylation with difunctional agents. Non-limiting mention may be made, for example, of adipic acid/dialkylaminohydroxyalkyldialkylenetriamine polymers in which the alkyl radical contains from 1 to 4 carbon atoms, such as a methyl, ethyl or propyl group. Such polymers are described, for example, in French Patent No. 1 583 363.

Among these derivatives, non-limiting mention may be made, for example, of the adipic acid/dimethylaminohydroxypropyl/diethylenetriamine polymers sold under the name "Cartaretine F, F4 or F8" by the company Sandoz.

(8) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid can range from 0.8:1 to 1.4:1; the polyamino amide resulting therefrom is reacted with epichlorohydrin in a molar ratio of epichlorohydrin relative to the secondary amine group of the polyamino amide ranging from 0.5:1 to 1.8:1. Such polymers are described, for example, in U.S. Pat. Nos. 3,227,615 and 2,961,347.

For instance, polymers of this type are sold under the name "Hercosett 57" by the company Hercules Inc. or alternatively under the name "PD 170" or "Delsette 101" by the company Hercules, in the case of the adipic acid/epoxypropyl/diethylenetriamine copolymer.

(9) Cyclopolymers of alkyldiallylamine or of dialkyldiallylammonium, such as the homopolymers or copolymers containing, as main constituent of the chain, units corresponding to formula (V) or (VI):

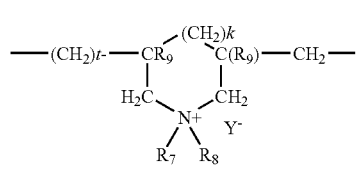

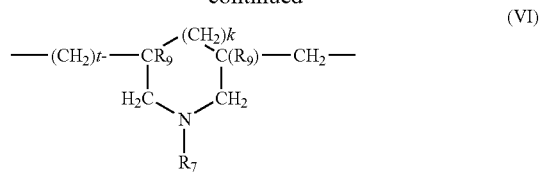

in which formulae (V) or (VI):

k and t are equal to 0 or 1, the sum k+t being equal to 1;

$R_9$ is chosen from a hydrogen atom and a methyl radical;

$R_7$ and $R_8$, independently of each other, are chosen from alkyl groups having from 1 to 6 carbon atoms, such as from 1 to 4 carbon atoms, hydroxyalkyl groups in which the alkyl group has 1 to 5 carbon atoms, for instance, a lower ($C_1$-$C_4$) amidoalkyl group; or alternatively, $R_7$ and $R_8$ are, together with the nitrogen atom to which they are attached, heterocyclic groups such as piperidyl or morpholinyl; and $Y^-$ is an anion such as bromide, chloride, acetate, borate, citrate, tartrate, bisulfate, bisulfite, sulfate or phosphate.

These polymers are described, for example, in French Patent No. 2 080 759 and in its Certificate of Addition 2 190 406.

Among the polymers defined above, non-limiting mention may be made of the dimethyldiallylammonium chloride homopolymer sold under the name "Merquat 100" by the company Calgon (and its homologues of low weight-average molecular mass) and the copolymers of diallyidimethylammonium chloride and of acrylamide, sold under the name "Merquat 550".

(10) The quaternary diammonium polymer containing repeating units corresponding to the formula:

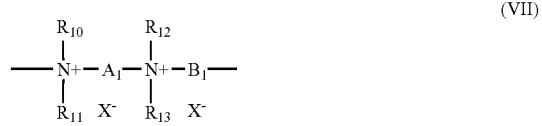

in which formula (VI):

$R_{10}$, $R_{11}$, $R_{12}$ and $R_{13}$, which may be identical or different, are chosen from aliphatic, alicyclic and arylaliphatic radicals comprising from 1 to 20 carbon atoms and from lower hydroxyalkylaliphatic radicals, or alternatively $R_{10}$, $R_{11}$, $R_{12}$ and $R_{13}$, together or separately, constitute, with the nitrogen atoms to which they are attached, heterocycles optionally containing a second hetero atom other than nitrogen, or alternatively $R_{10}$, $R_{11}$, $R_{12}$ and $R_{13}$ represent a linear or branched $C_1$-$C_6$ alkyl radical substituted with a nitrile, ester, acyl or amide group or a group —CO—O—$R_{14}$-D or —CO—NH—$R_{14}$-D where $R_{14}$ is an alkylene and D is a quaternary ammonium group;

$A_1$ and $B_1$ are polymethylene groups comprising from 2 to 20 carbon atoms which may be linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ is an anion derived from an inorganic or organic acid;

$A_1$, $R_{10}$ and $R_{12}$ can form, with the two nitrogen atoms to which they are attached, a piperazine ring; in addition, if $A_1$ is a linear or branched, saturated or unsaturated alkylene or hydroxyalkylene radical, then $B_1$ can also be a group —$(CH_2)_n$—CO-D-OC—$(CH_2)_n$—, wherein n ranges from 1 to 100, such as from 1 to 50, and D is chosen from:
a) a glycol residue of formula: —O-Z-O—, where Z is chosen from a linear or branched hydrocarbon-based radical or a group corresponding to one of the following formulae:

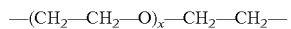

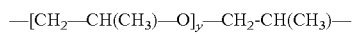

where x and y are integers ranging from 1 to 4, representing a defined and unique degree of polymerization or any number from 1 to 4 representing an average degree of polymerization;
b) a bis-secondary diamine residue such as a piperazine derivative;
c) a bis-primary diamine residue of formula: —NH—Y—NH—, where Y is a linear or branched hydrocarbon-based radical, or alternatively the divalent radical

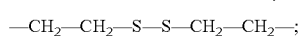

d) a ureylene group of formula: —NH—CO—NH—.

According to at least one embodiment as disclosed herein, $X^-$ is an anion such as chloride or bromide.

These polymers generally have a number-average molecular mass ranging from 1000 to 100,000.

Polymers of this type are described, for example, in French Patent Nos. 2 320 330; 2 270 846; 2 316 271; 2 336 434 and 2 413 907 and U.S. Pat. Nos. 2,273,780; 2,375,853; 2,388,614; 2,454,547; 3,206,462; 2,261,002; 2,271,378; 3,874,870; 4,001,432; 3,929,990; 3,966,904; 4,005,193; 4,025,617; 4,025,627; 4,025,653; 4,026,945; and 4,027,020.

For instance, it is possible to use polymers that comprise repeating units corresponding to the following formula (VIII):

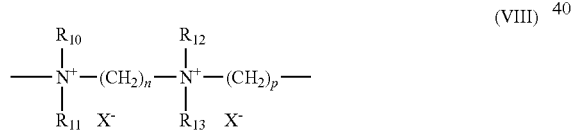

in which $R_{10}$, $R_{11}$, $R_{12}$ and $R_{13}$, which may be identical or different, are chosen from alkyl and hydroxyalkyl radicals comprising from 1 to 4 carbon atoms, n and p are integers ranging from 2 to 20, and $X^-$ is an anion derived from a mineral or organic acid.

(11) Polyquaternary ammonium polymers comprising of units of formula (IX)

in which p is an integer ranging from 1 to 6, D may be a bond or may be a group —$(CH_2)_r$—CO— in which r is a number equal to 4 or 7, and $X^-$ is an anion.

Such polymers may be prepared according to the processes described in U.S. Pat. Nos. 4,157,388; 4,702,906; and 4,719,282. For example, the polymers are described in European Patent Application No. EP-A-122 324.

Among these polymers, non-limiting examples that may be mentioned include the products "Mirapol A 15", "Mirapol AD1", "Mirapol AZ1" and "Mirapol 175" sold by the company Miranol.

(12) Quaternary polymers of vinylpyrrolidone and of vinylimidazole, for instance the products sold under the names LUVIQUAT FC 905, FC 550 and FC 370 by the company BASF.

(13) Polyamines such as POLYQUART H sold by Henkel, which is given under the reference name "Polyethylene glycol (15) tallow polyamine" in the CTFA Dictionary.

(14) Crosslinked methacryloyloxy($C_1$-$C_4$)alkyltri($C_1$-$C_4$) alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. A crosslinked acrylamide/methacryloyloxyethyltrimethylammonium chloride copolymer (20/80 by weight) in the form of a dispersion containing 50% by weight of the copolymer in mineral oil can be used, for example. This dispersion is sold under the name "Salcare® SC 92" by the company Allied Colloids. A crosslinked methacryloyloxyethyltrimethylammonium chloride homopolymer containing about 50% by weight of the homopolymer in mineral oil or in a liquid ester can also be used. These dispersions are sold under the names "Salcare® SC 95" and "Salcare® SC 96" by the company Allied Colloids.

(15) Other cationic polymers which can be used in the context of the present disclosure are polyalkyleneimines, for instance polyethyleneimines, polymers containing vinylpyridine or vinylpyridinium units, condensates of polyamines and of epichlorohydrin, quaternary polyureylenes and chitin derivatives.

Among all the cationic polymers which may be used in the context of the present disclosure, the polymers of families (1), (9), (10), (11) and (14) can be used, for example. Further, for instance the polymers containing repeating units of formulae (W) and (U) below can be used:

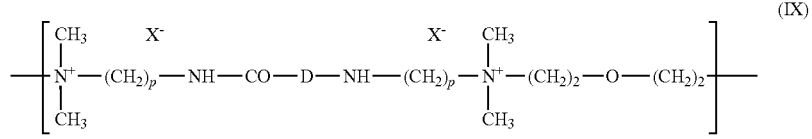

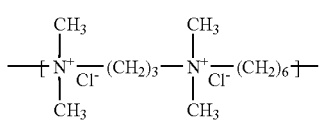

(W)

such as those whose molecular weight, determined by gel permeation chromatography, ranges from 9500 to 9900;

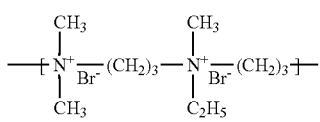

(U)

and for example those whose molecular weight, determined by gel permeation chromatography, is about 1200.

With respect to the amphoteric polymers that may be used in accordance with the present disclosure, they may be chosen from polymers comprising units K and M randomly distributed in the polymer chain, in which K is a unit derived from a monomer comprising at least one basic nitrogen atom and M is a unit derived from an acidic monomer comprising one or more carboxylic or sulfonic groups, or alternatively K and M may represent groups derived from zwitterionic carboxybetaine or sulfobetaine monomers;

K and M may also represent a cationic polymer chain comprising primary, secondary, tertiary or quaternary amine groups, in which at least one of the amine groups bears a carboxylic or sulfonic group linked via a hydrocarbon-based radical, or alternatively K and M form part of a chain of a polymer containing an α,β-dicarboxylic ethylene unit in which one of the carboxylic groups has been made to react with a polyamine comprising one or more primary or secondary amine groups.

As disclosed herein, for instance, the amphoteric polymers corresponding to the above definition can be chosen from the following polymers:

(1) polymers resulting from the copolymerization of a monomer derived from a vinyl compound bearing a carboxylic group such as, for example, acrylic acid, methacrylic acid, maleic acid, α-chloroacrylic acid, and from a substituted vinyl compound containing at least one basic atom, such as, for instance, dialkylaminoalkyl methacrylate and acrylate, dialkylaminoalkylmethacrylamide and -acrylamide. Such compounds are described in U.S. Pat. No. 3,836,537. Non-limiting mention may also be made of the sodium acrylate/acrylamidopropyltrimethylammonium chloride copolymer sold under the name POLYQUART KE 3033 by the company Henkel.

The vinyl compound may also be a dialkyldiallylammonium salt such as dimethyldiallylammonium chloride. The copolymers of acrylic acid and of the latter monomer are sold under the names MERQUAT 280, MERQUAT 295 and MERQUAT Plus 3330 by the company Calgon.

(2) Polymers containing units derived from:
  a) at least one monomer chosen from acrylamides and methacrylamides substituted on the nitrogen with an alkyl radical;
  b) at least one acidic comonomer containing one or more reactive carboxylic groups; and
  c) at least one basic comonomer such as esters containing primary, secondary, tertiary and quaternary amine substituents of acrylic and methacrylic acids and the product of quaternization of dimethylaminoethyl methacrylate with dimethyl or diethyl sulfate.

The N-substituted acrylamides or methacrylamides according to the present disclosure include but are not limited to groups in which the alkyl radicals contain from 2 to 12 carbon atoms such as N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen for example from acrylic acid, methacrylic acid, crotonic acid, itaconic acid, maleic acid and fumaric acid and alkyl monoesters, having 1 to 4 carbon atoms, of maleic or fumaric acids or anhydrides.

For instance, the basic comonomers include but are not limited to aminoethyl, butylaminoethyl, N,N'-dimethylaminoethyl and N-tert-butylaminoethyl methacrylates.

The copolymers whose CTFA (4th Edition, 1991) name is octylacrylamide/acrylates/butylaminoethyl methacrylate copolymer such as the products sold under the name AMPHOMER or LOVOCRYL 47 by the company National Starch can be used, for example.

(3) Polyamino amides that are crosslinked and alkylated partially or totally derived from polyamino amides of formula (X):

(X)

in which $R_{19}$ is a divalent radical derived from a saturated dicarboxylic acid, a mono- or dicarboxylic aliphatic acid containing an ethylenic double bond, an ester of a lower alkanol, having 1 to 6 carbon atoms, of these acids or a radical derived from the addition of any one of the acids to a bis (primary) or bis(secondary) amine, and Z is a bis(primary), mono- or bis(secondary) polyalkylene-polyamine radical, for example, and represents:

a) in amounts of from 60 to 100 mol %, the radical

(XI)

where x=2 and p=2 or 3, or alternatively x=3 and p=2 this radical being derived from diethylenetriamine, from triethylenetetraamine or from dipropylenetriamine;

b) in amounts of from 0 to 40 mol %, the radical (XI) above in which x=2 and p=1 and which is derived from ethylenediamine, or the radical derived from piperazine:

c) in amounts of from 0 to 20 mol %, the —NH—$(CH_2)_6$—NH— radical derived from hexamethylenediamine, these polyamino amines being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

The saturated carboxylic acids can be chosen for example from acids having 6 to 10 carbon atoms, such as adipic acid, 2,2,4-trimethyladipic acid and 2,4,4-trimethyladipic acid, terephthalic acid and acids containing an ethylenic double bond, for instance acrylic acid, methacrylic acid and itaconic acid.

The alkane sultones used in the alkylation include but are not limited to propane sultone or butane sultone, and the salts of the alkylating agents, for example, sodium or potassium salts can be used.

(4) Polymers containing zwitterionic units of formula:

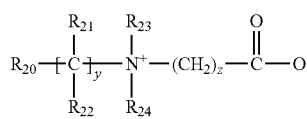
(XII)

in which $R_{20}$ is a polymerizable unsaturated group such as an acrylate, methacrylate, acrylamide or methacrylamide group, y and z are integers ranging from 1 to 3, $R_{21}$ and $R_{22}$ are a hydrogen atom, methyl, ethyl or propyl, $R_{23}$ and $R_{24}$ are a hydrogen atom or an alkyl radical such that the sum of the carbon atoms in $R_{23}$ and $R_{24}$ does not exceed 10.

The polymers comprising such units can also contain units derived from nonzwitterionic monomers such as dimethyl or diethylaminoethyl acrylate or methacrylate or alkyl acrylates or methacrylates, acrylamides or methacrylamides or vinyl acetate.

By way of example, non-limiting mention may be made of the copolymer of butyl methacrylate/dimethyl carboxymethylammonio ethyl methacrylate such as the product sold under the name DIAFORMER Z301 by the company Sandoz.

(5) Chitosan-based polymers comprising monomer units corresponding to formulae (XIII), (XIV) and (XV) below:

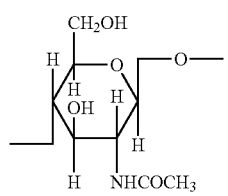
(XIII)

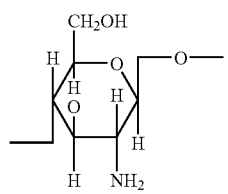
(XIV)

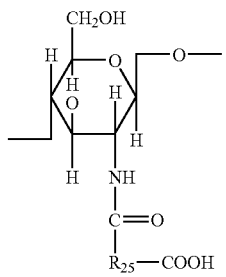
(XV)

the unit (XIII) being present in amounts ranging from 0 to 30%, the unit (XIV) in amounts ranging from 5% to 50% and the unit (XV) in amounts ranging from 30% to 90%, it being understood that, in this unit (XV), $R_{25}$ represents a radical of formula:

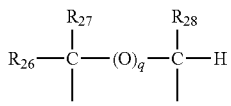

in which:
if q=0, $R_{26}$, $R_{27}$ and $R_{28}$, which may be identical or different, are each chosen from hydrogen atoms, methyl, hydroxyl, acetoxy and amino residues, monoalkylamine residues, and dialkylamine residues which are optionally interrupted by at least one nitrogen atom and/or optionally substituted with at least one group chosen from amine, hydroxyl, carboxyl, alkylthio and sulfonic groups, alkylthio residues in which the alkyl group bears an amino residue, at least one of the radicals $R_{26}$, $R_{27}$ and $R_{28}$ being, in this case, a hydrogen atom; or
if q=1, $R_{26}$, $R_{27}$ and $R_{28}$ each are a hydrogen atom, and also the salts formed by these compounds with bases or acids.

(6) Polymers derived from the N-carboxyalkylation of chitosan, such as N-carboxymethylchitosan or N-carboxybutylchitosan sold under the name "Evalsan" by the company Jan Dekker.

(7) Polymers corresponding to the general formula (XVI) such as those described, for example, in French Patent No. 1 400 366:

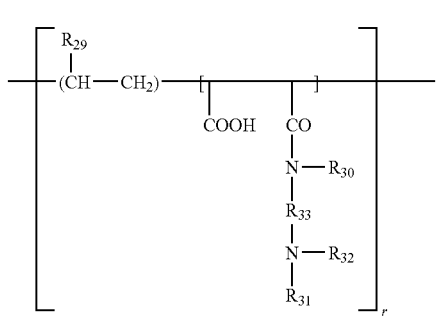
(XVI)

in which $R_{29}$ is chosen from a hydrogen atom, a $CH_3O$, $CH_3CH_2O$ and a phenyl radical, $R_{30}$ is chosen from hydrogen and a lower alkyl radical such as methyl or ethyl, $R_{31}$ is chosen from a hydrogen and a lower alkyl radical such as methyl or ethyl, $R_{32}$ is chosen from a lower alkyl radical such as methyl or ethyl and a radical corresponding to the formula: —$R_{33}$—N($R_{31}$)$_2$, $R_{33}$ representing a —CH$_2$—CH$_2$—, —CH$_2$—CH$_2$—CH$_2$— or —CH$_2$—CH(CH$_3$)— group, $R_{31}$ having the meanings mentioned above, and r being a number greater than 1, and also the higher homologues of these radicals and containing up to 6 carbon atoms.

(8) Amphoteric polymers of the type -D-X-D-X— chosen from:
  a) polymers obtained by the action of chloroacetic acid or sodium chloroacetate on compounds containing at least one unit of formula:

-D-X-D-X-D- (XVII)

where D is a radical:

and X is the symbol E or E', E or E', which may be identical or different, is a divalent radical which is an alkylene radical with a straight or branched chain containing up to 7 carbon atoms in the main chain, which is unsubstituted or substituted with hydroxyl groups and which can contain, in addition to the oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups;
  b) polymers of formula:

-D-X-D-X— (XVIII)

where D is a radical:

and X is the symbol E or E' and at least once E'; E having the meaning given above and E' being a divalent radical which is an alkylene radical with a straight or branched chain having up to 7 carbon atoms in the main chain, which is unsubstituted or substituted with one or more hydroxyl radicals and containing one or more nitrogen atoms, the nitrogen atom being substituted with an alkyl chain which is optionally interrupted with an oxygen atom and necessarily containing one or more carboxyl functions or one or more hydroxyl functions and betainized by reaction with chloroacetic acid or sodium chloroacetate.

(9) ($C_1$-$C_5$)alkyl vinyl ether/maleic anhydride copolymers partially modified by semi-amidation with an N,N-dialkylaminoalkylamine such as N,N-dimethylaminopropylamine or by semi-esterification with an N,N-dialkanolamine. These copolymers can also contain other vinyl comonomers such as vinylcaprolactam.

In at least one embodiment, the amphoteric polymers that can be used according to the present disclosure are those of family (1).

According to the present disclosure, the cationic or amphoteric substantive polymer(s), when they are present, may be present in an amount ranging from 0.01% to 10% by weight, relative to the total weight of the dye composition, such as from 0.05% to 5% by weight, relative to the total weight of the dye composition and further, for example from 0.1% to 3% by weight, relative to the total weight of the dye composition.

Dyeing Medium

The medium that is suitable for dyeing keratin fibers comprises water or a mixture of water and of at least one organic solvent to dissolve the compounds that are not sufficiently water-soluble. Non-limiting examples of organic solvents include $C_1$-$C_4$ lower alkanols, such as ethanol and isopropanol; polyols and polyol ethers, for instance 2-butoxyethanol, propylene glycol, propylene glycol monomethyl ether, diethylene glycol monoethyl ether and monomethyl ether, and also aromatic alcohols, for instance benzyl alcohol or phenoxyethanol, and mixtures thereof.

The solvents may be present in proportions ranging from 1% to 40% by weight, relative to the total weight of the dye composition, and further ranging from 5% to 30% by weight, relative to the total weight of the dye composition.

Additives

The composition may also comprise additives that are common in the field, such as, for example, organic thickeners other than the hydroxyethylcellulose described above, or mineral thickeners; antioxidants; penetrants; sequestrants; fragrances; buffers; dispersants; conditioning agents other than the cationic or amphoteric substantive polymers, for instance cations, or volatile or non-volatile, modified or unmodified silicones; film-forming agents; ceramides; preserving agents; stabilizers; opacifiers.

Needless to say, a person skilled in the art will take care to select this or these optional additional compound(s) such that the beneficial properties intrinsically associated with the composition in accordance with the present disclosure are not, or are not substantially, adversely affected by the envisaged addition(s).

Processes

As indicated previously, the present disclosure also relates to a process for dyeing keratin materials using the composition according to the present disclosure.

According to at least one embodiment, the process comprises applying the dye composition as disclosed herein, in the absence of an oxidizing agent, to keratin materials, wherein the keratin fibers may be wet or dry, with or without a final rinsing of the composition.

In the case of the above-mentioned embodiment, the composition according to the present disclosure does not comprise any oxidation dye precursor, but only at least one direct dye.

According to another embodiment of the present disclosure, the process comprises applying the dye composition according to the present disclosure, in the presence of an oxidizing agent, wherein the keratin fibers may be wet or dry, and then leaving the composition on the keratin fibers for a period that is sufficient to obtain the desired coloration.

According to another aspect of the present disclosure, the dye composition as disclosed herein and an oxidizing composition can be applied to the keratin fibers simultaneously or successively without intermediate rinsing.

For instance, the composition applied is a "ready-to-use composition", i.e. a composition obtained by extemporaneous mixing of the dye composition according to the present disclosure with a composition comprising at least one oxidizing agent.

In this case, the at least one dye composition may comprise one or more oxidation dye precursors. It may also comprise at least one direct dye, when lightening of the keratin fibers is desired in combination with dyeing.

Obviously, the dye composition may comprise a combination of oxidation dye precursors and of direct dyes.

The at least one oxidizing agent present in the oxidizing composition may be chosen, for example, from hydrogen peroxide, urea peroxide, alkali metal bromates, persalts such as perborates and persulfates, and enzymes such as peroxidases and two-electron or four-electron oxidoreductases. In one embodiment, hydrogen peroxide is the oxidizing agent used.

The amount of oxidizing agent present In the composition may range from 1% to 40% by weight, relative to the total weight of the ready-to-use composition, such as from 1% to 20% by weight, relative to the total weight of the ready-to-use composition.

Generally, the oxidizing composition used is an aqueous composition and may be in the form of a solution or an emulsion.

Usually, the composition free of oxidizing agent is mixed with about 0.5 to 10 weight equivalents of the oxidizing composition.

It should be noted that the pH of the ready-to-use composition may range from 3 to 12, for instance from 4 to 11 and even further, for example from 6.5 to 10.5.

The pH of the ready-to-use composition may be adjusted using a basifying or acidifying agent that can be chosen, for example, from those mentioned previously.

Still in the case where the composition is applied in the presence of an oxidizing agent, the process may comprise a preliminary step that comprises separately storing, on the one hand, at least one dye composition according to the present disclosure and, on the other hand, a composition comprising at least one oxidizing agent in a medium that is suitable for dyeing human keratin fibers, and then in mixing them together at the time of use, before applying this mixture to the wet or dry keratin materials.

Irrespective of the embodiment adopted, i.e. in the presence or absence of oxidizing agent, the time required to develop the coloration is from about a few seconds to 60 minutes such as from about 1 to 50 minutes.

The temperature required to develop the coloration ranges from room temperature (15 to 25° C.) to 250° C., for instance from room temperature to 180° C. and further, for example, from room temperature to 60° C.

Once the time required to develop the coloration has elapsed, the composition can be removed.

This may take place in a conventional manner, either by performing at least one rinsing operation, or by performing one or more washing and rinsing operations, or by performing a combination thereof. Finally, the keratin materials are dried or are left to dry.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in its respective testing measurement.

The examples that follow are intended to illustrate the present disclosure without, however, being limiting in nature.

EXAMPLES

Example 1

The alkaline dye composition A below was prepared (amounts expressed in grams):

|  | Amount (g %) |
|---|---|
| Oleic acid | 2 |
| Pure monoethanolamine | 0.47 |
| Oxyethylenated (30 OE) oleocetyl alcohol | 3.15 |
| Oxyethylenated (12 OE) lauryl alcohol | 4.4 |
| Oxyethylenated (5 OE) decyl alcohol | 3.15 |
| Oxyethylenated (3 OE) decyl alcohol | 12 |
| Oleyl alcohol | 1.8 |
| Coconut acid monoisopropanolamide | 4 |
| Hydroxyethylcellulose (MW: 1 300 000; Natrosol 250 HHR; from Aqualon (Hercules)) | 0.2 |
| Hydroxyethylcellulose quaternized with substituted lauryldimethylammonium epoxide (Polyquaternium-24; Quatrisoft LM 200; from Amerchol) | 0.15 |
| Glycerol | 3 |
| Polydimethyldiallylammonium chloride at 40% in water (Polyquaternium-6) | 3 |
| Ascorbic acid | 0.25 |
| EDTA | 0.2 |
| Ammonium thiolactate as an aqueous 58% solution | 0.8 |
| Aqueous ammonia (20% ammonia) | 8 |
| 1-Hydroxy-4-aminobenzene | 0.545 |
| 1-Methyl-2-hydroxy-4-aminobenzene | 0.615 |
| Fragrance | 0.95 |
| Deionized water | 51.32 |

Dye composition A was stable on storage.

Dye composition A was mixed, at the time of use, in a plastic bowl and for 2 minutes, with an aqueous oxidizing composition containing 6% hydrogen peroxide, at a rate of 1 part of dye composition per 1.5 parts of oxidizing composition. The mixing was quick and easy.

The mixture obtained was applied to locks of natural hair containing 90% white hairs, and was left on for 20 minutes. The application was quick and easy. The product stayed in place perfectly, did not run, and spread well from the root to the end.

The locks were then rinsed with water, washed with a standard shampoo, rinsed again with water, and then dried and disentangled. The mixture was satisfactorily removed on rinsing.

The hair was dyed in a strong coppery red shade.

Furthermore, the hair was not coarse.

Example 2

The alkaline dye compositions below were prepared (amounts expressed in grams):

|  | Composition B (inventive) | Comparative Composition C |
|---|---|---|
| Oleic acid | 2 | 2 |
| Pure monoethanolamine | 0.47 | 0.47 |
| Oxyethylenated (30 OE) oleocetyl alcohol | 3.15 | 4.5 |
| Oxyethylenated (12 OE) lauryl alcohol | 4.4 | 6.3 |
| Oxyethylenated (5 OE) decyl alcohol | 3.15 | 4.5 |
| Oxyethylenated (3 OE) decyl alcohol | 12 | 17.2 |
| Oleyl alcohol | 1.8 | 1.8 |
| Coconut acid monoisopropanolamide | 4 | 4 |
| Hydroxyethylcellulose (MW: 1 300 000; Natrosol 250 HHR; from Aqualon (Hercules)) | 0.2 | / |
| Hydroxyethylcellulose quaternized with substituted lauryldimethylammonium epoxide (Polyquaternium-24; Quatrisoft LM 200; from Amerchol) | 0.15 | 0.15 |
| Glycerol | 3 | 3 |
| Tetramethylhexamethylenediamine/1,3-dichloropropylene polycondensate as an aqueous 60% solution | 2 | 2 |
| Polydimethyldiallylammonium chloride at 40% in water, non-stabilized (Polyquaternium-6) | 2 | 2 |
| Ascorbic acid | 0.25 | 0.25 |
| EDTA | 0.2 | 0.2 |
| Ammonium thiolactate as an aqueous 58% solution | 0.8 | 0.8 |
| Aqueous ammonia (20% ammonia) | 8 | 8 |
| 1-Hydroxy-4-aminobenzene | 0.545 | 0.545 |
| 1-Methyl-2-hydroxy-4-aminobenzene | 0.615 | 0.615 |
| Fragrance | 0.95 | 0.95 |
| Deionized water | 50.32 | 40.72 |

Dye compositions B and C were stable on storage.

Dye compositions B and C were mixed, at the time of use, in a plastic bowl and for 2 minutes, with an aqueous oxidizing composition containing 6% hydrogen peroxide, at a rate of 1 part of dye composition per 1.5 parts of oxidizing composition. The mixing was quick and easy, even more so for composition B.

Each mixture obtained was applied to locks of natural hair containing 90% white hairs, and was left on for 20 minutes.

It is noted that composition B stayed in place perfectly, did not run, and spread better from the root to the end, as compared with composition C.

Each lock was then rinsed with water, washed with a standard shampoo, rinsed again with water and then dried and disentangled.

The mixtures were satisfactorily removed on rinsing.

In the case of the two compositions, the hair was dyed in a strong coppery red shade.

The shade was slightly stronger and less selective with composition B according to the present disclosure, when compared with composition C.

Furthermore, the hair was less coarse with the mixture derived from composition B according to the present disclosure, when compared with composition C.

Example 3

The ammonia-free dye composition D below was prepared (amounts expressed in grams):

|  | Composition D |
|---|---|
| Oleic acid | 2 |
| Pure monoethanolamine | 4.72 |
| Oleocetyl alcohol(30 OE) | 3.15 |
| Oxyethylenated (12 OE) lauryl alcohol | 4.4 |
| Oxyethylenated (5 OE) decyl alcohol | 3.15 |
| Oxyethylenated (3 OE) decyl alcohol | 12 |
| Oleyl alcohol | 1.8 |
| Coconut acid monoisopropanolamide | 2 |
| Hydroxyethylcellulose (MW: 1 300 000) sold under the trade name Natrosol 250 HHR; from Aqualon (Hercules) | 0.3 |
| Hydroxyethylcellulose quaternized with substituted lauryldimethylammonium epoxide (Polyquaternium-24) sold under the trade name Quatrisoft LM 200; from Amerchol | 0.2 |
| Glycerol | 3 |
| Tetramethylhexamethylenediamine/1,3-dichloropropylene polycondensate as an aqueous 60% solution | 3 |
| Polydimethyldiallylammonium chloride at 40% in water, non-stabilized (Polyquaternium-6) | 3 |
| Ascorbic acid | 0.25 |
| EDTA | 0.2 |
| Sodium metabisulfite | 0.46 |
| Anhydrous sodium metasilicate | 2 |
| 1-Hydroxy-4-aminobenzene | 0.545 |
| 1-Methyl-2-hydroxy-4-aminobenzene | 0.615 |
| Fragrance | 0.95 |
| Deionized water | 52.26 |

Dye composition D was mixed, at the time of use, in a plastic bowl and for 2 minutes, with an aqueous oxidizing composition containing 6% aqueous hydrogen peroxide solution, at a rate of 1 part of dye composition per 1.5 parts of oxidizing composition. The mixing was quick and easy.

The mixture obtained was applied to locks of natural hair containing 90% white hairs and was left on for 20 minutes. The application was quick and easy. The product stayed in place perfectly, did not run, and spread well from the root to the end.

The locks were then rinsed with water, washed with a standard shampoo, rinsed again with water and then dried and disentangled. The mixture was satisfactorily removed on rinsing.

The hair was dyed in a strong coppery red shade. Furthermore, the hair was not coarse.

Example 4

The ammonia-free dye composition E below was prepared (amounts expressed in grams):

|  | Composition E |
|---|---|
| Oleic acid | 2 |
| Pure monoethanolamine | 0.47 |
| Oxyethylenated (30 OE) oleocetyl alcohol | 3.15 |
| Oxyethylenated (12 OE) lauryl alcohol | 4.4 |
| Oxyethylenated (5 OE) decyl alcohol | 3.15 |
| Oxyethylenated (3 OE) decyl alcohol | 12 |
| Oleyl alcohol | 1.8 |
| Coconut acid monoisopropanolamide | 2 |
| Hydroxyethylcellulose (MW: 1 300 000) sold under the trade name Natrosol 250 HHR; from Aqualon (Hercules) | 0.3 |
| Hydroxyethylcellulose quaternized with substituted lauryldimethylammonium epoxide (Polyquaternium-24) sold under the trade name Quatrisoft LM 200; from Amerchol | 0.2 |
| Glycerol | 3 |

-continued

| | Composition E |
|---|---|
| Tetramethylhexamethylenediamine/1,3-dichloropropylene polycondensate as an aqueous 60% solution | 3 |
| Polydimethyldiallylammonium chloride at 40% in water, non-stabilized (Polyquaternium-6) | 3 |
| Ascorbic acid | 0.25 |
| EDTA | 0.2 |
| Sodium metabisulfite | 0.46 |
| 1-Hydroxy-4-aminobenzene | 0.545 |
| 1-Methyl-2-hydroxy-4-aminobenzene | 0.615 |
| Fragrance | 0.95 |
| Deionized water | 48.51 |

Dye composition E was mixed, at the time of use, in a plastic bowl and for 2 minutes, with an aqueous oxidizing composition containing 6% aqueous hydrogen peroxide solution, at a rate of 1 part of dye composition per 1.5 parts of oxidizing composition. The mixing was quick and easy.

The mixture obtained was applied to locks of natural hair containing 90% white hairs and was left on for 20 minutes. The application was quick and easy. The product stayed in place perfectly, did not run, and spread well from the root to the end.

The locks were then rinsed with water, washed with a standard shampoo, rinsed again with water and then dried and disentangled. The mixture was satisfactorily removed on rinsing.

The hair was dyed in a strong coppery red shade. Furthermore, the hair was not coarse.

What is claimed is:

1. A dye composition comprising, in a medium that is suitable for dyeing keratin fibers:
    at least one dye chosen from oxidation dye precursors and direct dyes;
    at least one surfactant chosen from nonionic surfactants and anionic surfactants;
    at least one hydroxyethylcellulose;
    at least one cationic associative polymer; and
    at least one fatty substance;
    wherein the weight ratio of the total amount of the at least one surfactant chosen from nonionic surfactants and anionic surfactants to the total amount of the at least one fatty substance is greater than or equal to 1.75; and
    wherein the dye composition comprises water in an amount of at least 40% by weight, relative to the total weight of the dye composition.

2. The dye composition according to claim 1, wherein the dye composition comprises water in an amount of at least 45% by weight, relative to the total weight of the dye composition.

3. The dye composition according to claim 1, wherein the amount of water in the dye composition is at least 50% by weight, relative to the total weight of the dye composition.

4. The dye composition according to claim 1, wherein the at least one nonionic surfactant is chosen from:
    oxyalkylenated or glycerolated fatty alcohols;
    oxyalkylenated alkylphenols in which the alkyl chain is of $C_8$-$C_{18}$;
    oxyalkylenated or glycerolated fatty amides;
    oxyalkylenated plant oils;
    optionally oxyalkylenated fatty acid esters of sorbitan;
    optionally oxyalkylenated fatty acid esters of sucrose;
    fatty acid esters of polyethylene glycol;
    ($C_6$-$C_{30}$)alkylpolyglycosides;
    N—($C_6$-$C_{30}$)alkylglucamine derivatives;
    amine oxides; and
    copolymers of ethylene oxide and of propylene oxide.

5. The dye composition according to claim 1, wherein said amine oxides are chosen from ($C_{10}$-$C_{14}$)alkylamine oxides and N-acylaminopropylmorpholine oxides.

6. The dye composition according to claim 1, wherein the at least one nonionic surfactant is chosen from oxyalkylenated or glycerolated fatty alcohols.

7. The dye composition according to claim 1, wherein the at least one anionic surfactant is chosen from:
    ($C_6$-$C_{30}$)alkyl sulfates, ($C_6$-$C_{30}$)alkyl ether sulfates, ($C_6$-$C_{30}$)alkylamido ether sulfates, alkylaryl polyether sulfates, monoglyceride sulfates;
    ($C_6$-$C_{30}$)alkylsulfonates, ($C_6$-$C_{30}$)alkylamide sulfonates, ($C_6$-$C_{30}$)alkylaryl sulfonates, α-olefin sulfonates, paraffin sulfonates;
    ($C_6$-$C_{30}$)alkyl phosphates;
    ($C_6$-$C_{30}$)alkyl sulfosuccinates, ($C_6$-$C_{30}$)alkyl ether sulfosuccinates, ($C_6$-$C_{30}$)alkylamide sulfosuccinates;
    ($C_6$-$C_{30}$)alkyl sulfoacetates;
    ($C_6$-$C_{24}$)acyl sarcosinates;
    ($C_6$-$C_{24}$)acyl glutamates;
    ($C_6$-$C_{30}$)alkylpolyglycoside carboxylic ethers; ($C_6$-$C_{30}$) alkylpolyglycoside sulfosuccinates;
    ($C_6$-$C_{30}$)alkyl sulfosuccinamates;
    ($C_6$-$C_{24}$)acyl isethionates;
    N-($C_6$-$C_{24}$)acyl taurates;
    $C_6$-$C_{30}$ fatty acid salts; coconut oil acid salts or hydrogenated coconut oil acid salts;
    ($C_8$-$C_{20}$)acyl lactylates;
    ($C_6$-$C_{30}$)alkyl-D-galactoside uronic acid salts; and
    polyoxyalkylenated ($C_6$-$C_{30}$)alkyl ether carboxylic acid salts, polyoxyalkylenated ($C_6$-$C_{30}$)alkylaryl ether carboxylic acid salts, polyoxyalkylenated ($C_6$-$C_{30}$)alkylamido ether carboxylic acid salts.

8. The dye composition according to claim 1, wherein the at least one surfactant chosen from nonionic surfactants and anionic surfactants is present in an amount ranging from 0.01% to 50% by weight, relative to the total weight of the dye composition.

9. The dye composition according to claim 1, wherein the at least one fatty substance is chosen from non-oxyalkylenated, non-glycerolated fatty alcohols, non-oxyalkylenated, non-glycerolated fatty acid amides, carboxylic acid monoesters and polyesters, mineral oils and plant oils, and mixtures thereof.

10. The dye composition according to claim 1, wherein the at least one fatty substance is present in an amount less than or equal to 10% by weight, relative to the total weight of the dye composition.

11. The dye composition according to claim 1, wherein the weight ratio of the total amount of the at least one surfactant to the amount of the at least one fatty substance is greater than 2.

12. The dye composition according to claim 1, wherein the weight ratio of the total amount of the at least one surfactant to the amount of the at least one fatty substance is less than 20.

13. The dye composition according to claim 1, wherein the at least one hydroxyethylcellulose has an average molecular weight of at least 700,000.

14. The dye composition according to claim 1, wherein the at least one hydroxyethylcellulose is present in an amount ranging from 0.01% to 5% by weight, relative to the total weight of the dye composition.

15. The dye composition according to claim 1, wherein the at least one cationic associative polymer is chosen from quaternized cellulose derivatives, cationic polyurethanes, cationic polyvinyllactams and cationic acrylic terpolymers.

16. The dye composition according to claim 1, wherein the at least one cationic associative polymer is present in an amount ranging from 0.01% to 5% by weight, relative to the total weight of the dye composition.

17. The dye composition according to claim 1, wherein the at least one oxidation dye precursor is chosen from at least one oxidation base and/or at least one coupler.

18. The dye composition according to claim 17, wherein the at least one oxidation base is present in an amount ranging from 0.0005% to 12% by weight, relative to the total weight of the dye composition.

19. The dye composition according to claim 16, wherein the at least one coupler is present in an amount ranging from 0.0001% to 15% by weight, relative to the total weight of the dye composition.

20. The dye composition according to claim 1, wherein the at least one direct dye is present in an amount ranging from 0.0005% to 15% by weight, relative to the total weight of the dye composition.

21. The dye composition according to claim 1, wherein the dye composition further comprises at least one basifying agent.

22. The dye composition according to claim 21, wherein the at least one basifying agent is chosen from aqueous ammonia, alkanolamines and combinations of $C_2$-$C_{10}$ alkanolamines with alkali metal or alkaline-earth metal silicates.

23. The dye composition according to claim 1, wherein the dye composition comprises at least one substantive polymer chosen from cationic substantive polymers and amphoteric substantive polymers.

24. The dye composition according to claim 23, wherein the at least one substantive polymer is present in an amount ranging from 0.01% to 10% by weight, relative to the total weight of the dye composition.

25. The dye composition according to claim 1, wherein the dye composition further comprises at least one oxidizing agent.

26. A process for dyeing keratin fibers, comprising applying to wet or dry keratin fibers a dye composition comprising, in a medium that is suitable for dyeing keratin fibers:
  at least one dye chosen from oxidation dye precursors and direct dyes;
  at least one surfactant chosen from nonionic surfactants and anionic surfactants;
  at least one hydroxyethylcellulose;
  at least one cationic associative polymer; and
  at least one fatty substance;
  wherein the weight ratio of the total amount of the at least one surfactant chosen from nonionic surfactants and anionic surfactants to the total amount of the at least one fatty substance is greater than or equal to 1.75; and
  wherein the dye composition comprises water in an amount of at least 40% by weight, relative to the total weight of the dye composition.

27. A process for dyeing keratin fibers, comprising
applying a dye composition to wet or dry keratin fibers in the presence of an oxidizing composition, which is applied simultaneously with or successively to the dye composition without intermediate rinsing;
leaving the mixture on the keratin fibers until a desired coloration is achieved; and
rinsing the keratin fibers,
wherein said dye composition comprises, in a medium that is suitable for dyeing keratin fibers:
  at least one dye chosen from oxidation dye precursors and direct dyes;
  at least one surfactant chosen from nonionic surfactants and anionic surfactants;
  at least one hydroxyethylcellulose;
  at least one cationic associative polymer; and
  at least one fatty substance;
  wherein the weight ratio of the total amount of the at least one surfactant chosen from nonionic surfactants and anionic surfactants to the total amount of the at least one fatty substance is greater than or equal to 1.75; and
  wherein the dye composition comprises water in an amount of at least 40% by weight, relative to the total weight of the dye composition.

28. A process for dyeing keratin fibers, comprising
applying a dye composition to wet or dry keratin fibers in the presence of an oxidizing composition, which is mixed with the dye composition before application;
leaving the mixture on the keratin fibers until a desired coloration is achieved; and
rinsing the keratin fibers,
wherein said dye composition comprises, in a medium that is suitable for dyeing keratin fibers:
  at least one dye chosen from oxidation dye precursors and direct dyes;
  at least one surfactant chosen from nonionic surfactants and anionic surfactants;
  at least one hydroxyethylcellulose;
  at least one cationic associative polymer; and
  at least one fatty substance;
  wherein the weight ratio of the total amount of the at least one surfactant chosen from nonionic surfactants and anionic surfactants to the total amount of the at least one fatty substance is greater than or equal to 1.75; and
  wherein the dye composition comprises water in an amount of at least 40% by weight, relative to the total weight of the dye composition.

29. A multi-compartment kit for dyeing keratin fibers, comprising:
  a first compartment that comprises at least one dye composition comprising, in a medium that is suitable for dyeing keratin fibers:
    at least one dye chosen from oxidation dye precursors and direct dyes;
    at least one surfactant chosen from nonionic surfactants and anionic surfactants;
    at least one hydroxyethylcellulose;
    at least one cationic associative polymer; and
    at least one fatty substance;
    wherein the weight ratio of the total amount of the at least one surfactant chosen from nonionic surfactants and anionic surfactants to the total amount of the at least one fatty substance is greater than or equal to 1.75; and
    wherein the dye composition comprises water in an amount of at least 40% by weight, relative to the total weight of the dye composition; and
  a second compartment that comprises at least one oxidizing composition.

* * * * *